US011998589B2

(12) United States Patent
Lewis et al.

(10) Patent No.: US 11,998,589 B2
(45) Date of Patent: Jun. 4, 2024

(54) PEGYLATED PEPTIDE AMPHIPHILE NANOFIBERS AND METHODS OF USE

(71) Applicant: Northwestern University, Evanston, IL (US)

(72) Inventors: Jacob A. Lewis, Chicago, IL (US); Ronit Freeman, Chapel Hill, NC (US); Samuel I. Stupp, Chicago, IL (US)

(73) Assignee: Northwestern University, Evanston, IL (US)

( * ) Notice: Subject to any disclaimer, the term of this patent is extended or adjusted under 35 U.S.C. 154(b) by 183 days.

(21) Appl. No.: 17/374,287

(22) Filed: Jul. 13, 2021

(65) Prior Publication Data

US 2022/0008509 A1 Jan. 13, 2022

Related U.S. Application Data

(60) Provisional application No. 63/051,043, filed on Jul. 13, 2020.

(51) Int. Cl.
| | | |
|---|---|---|
| *A61K 38/18* | (2006.01) | |
| *A61K 9/70* | (2006.01) | |
| *A61K 47/54* | (2017.01) | |
| *A61K 47/60* | (2017.01) | |
| *A61K 47/64* | (2017.01) | |

(52) U.S. Cl.
CPC ............ *A61K 38/1841* (2013.01); *A61K 9/70* (2013.01); *A61K 47/54* (2017.08); *A61K 47/60* (2017.08); *A61K 47/64* (2017.08); *A61K 47/645* (2017.08)

(58) Field of Classification Search
CPC .. A61K 38/1841; A61K 47/645; A61K 47/64; A61K 47/54; A61K 47/60; A61K 9/70
See application file for complete search history.

(56) References Cited

U.S. PATENT DOCUMENTS

| | | |
|---|---|---|
| 7,030,167 B2 | 4/2006 | Gunther |
| 7,371,719 B2 | 5/2008 | Stupp et al. |
| 7,452,679 B2 | 11/2008 | Stupp et al. |
| 7,491,690 B2 | 2/2009 | Stupp et al. |
| 7,534,761 B1 | 5/2009 | Stupp et al. |
| 7,544,661 B2 | 6/2009 | Stupp et al. |
| 7,554,021 B2 | 6/2009 | Stupp et al. |
| 7,683,025 B2 | 3/2010 | Stupp et al. |
| 7,745,708 B2 | 6/2010 | Stupp et al. |
| 7,838,491 B2 | 11/2010 | Stupp et al. |
| 7,851,445 B2 | 12/2010 | Stupp et al. |
| 8,063,014 B2 | 11/2011 | Stupp et al. |
| 8,076,295 B2 | 12/2011 | Hulvat et al. |
| 8,080,262 B2 | 12/2011 | Lee et al. |
| 8,114,834 B2 | 2/2012 | Hsu et al. |
| 8,114,835 B2 | 2/2012 | Mata et al. |
| 8,124,583 B2 | 2/2012 | Stupp et al. |
| 8,138,140 B2 | 3/2012 | Stupp et al. |
| 8,236,800 B2 | 8/2012 | Degrado et al. |
| 8,450,271 B2 * | 5/2013 | Shah ................... C07K 7/06 514/8.9 |
| 8,512,693 B2 | 8/2013 | Capito et al. |
| 8,546,338 B2 | 10/2013 | Donners et al. |
| 8,580,923 B2 | 11/2013 | Stupp et al. |
| 8,748,569 B2 | 6/2014 | Stupp et al. |
| 8,772,228 B2 | 7/2014 | Stupp et al. |
| 9,011,914 B2 | 4/2015 | Wong Po Foo et al. |
| 9,040,626 B2 | 5/2015 | Chien et al. |
| 9,044,514 B2 | 6/2015 | Xu et al. |

OTHER PUBLICATIONS

Behanna et al., Coassembly of amphiphiles with opposite peptide polarities into nanofibers. J Am Chem Soc. Feb. 2, 2005;127(4):1193-200.
Chen et al., Peptide hydrogels assembled from nonionic alkyl-polypeptide amphiphiles prepared by ring-opening polymerization. Biomacromolecules. Aug. 12, 2013;14(8):2494-8.
Clemons et al., Manipulating Cellular Interactions of Poly(glycidyl methacrylate) Nanoparticles Using Mixed Polymer Brushes. ACS Macro Letters 2016, 5 (10), 1132-1136.
Cui et al., Self-assembly of giant peptide nanobelts. Nano Lett. Mar. 2009;9(3):945-51.
Cui et al., Spontaneous and x-ray-triggered crystallization at long range in self-assembling filament networks. Science. Jan. 29, 2010;327(5965):555-9.
Edelbrock et al., Supramolecular Nanostructure Activates TrkB Receptor Signaling of Neuronal Cells by Mimicking Brain-Derived Neurotrophic Factor. Nano Lett. Oct. 10, 2018;18(10):6237-6247.
Elci et al., Surface Charge Controls the Suborgan Biodistributions of Gold Nanoparticles. ACS Nano. May 24, 2016;10(5):5536-42.
Freeman et al., Reversible self-assembly of superstructured networks. Science. Nov. 16, 2018;362(6416):808-813.
Fröhlich. The role of surface charge in cellular uptake and cytotoxicity of medical nanoparticles. Int J Nanomedicine. 2012;7:5577-91.
Gao et al., Electrostatic Control of Polymorphism in Charged Amphiphile Assemblies. J Phys Chem B. Feb. 23, 2017;121(7):1623-1628.
Goldberger et al., Electrostatic control of bioactivity. Angew Chem Int Ed Engl. Jul. 4, 2011;50(28):6292-5.
Greenfield et al., Tunable mechanics of peptide nanofiber gels. Langmuir. Mar. 2, 2010;26(5):3641-7.

(Continued)

*Primary Examiner* — Michael P Cohen
(74) *Attorney, Agent, or Firm* — Casimir Jones, S.C.; Rikki A. Hullinger

(57) ABSTRACT

Provided herein are peptide amphiphiles (PAs). In some embodiments, provided herein are PEGylated PAs (e.g. nonionic PAs). In some embodiments, the peptide amphiphiles are assembled into nanofibers. The nanofibers may further comprise a growth factor protein, which may bind to a growth factor binding sequence presented on the nonionic PA. In some embodiments, the nanofibers further comprise a charged peptide amphiphile. The charged peptide amphiphile may be bound to a growth factor protein. Further provided herein are methods of use of the peptide amphiphiles and compositions comprising the same, such as for regenerative therapy.

20 Claims, 23 Drawing Sheets

Specification includes a Sequence Listing.

(56) References Cited

OTHER PUBLICATIONS

Griffin et al., Photodegradable Macromers and Hydrogels for Live Cell Encapsulation and Release. J Am Chem Soc. Aug. 8, 2012;134(31):13103-7.
Hadjidemetriou et al., Nanomedicine: Evolution of the nanoparticle corona. Nat Nanotechnol. Apr. 6, 2017;12(4):288-290.
Hamley et al., Coassembly in binary mixtures of peptide amphiphiles containing oppositely charged residues. Langmuir. Apr. 23, 2013;29(16):5050-9.
Hamley et al., Solution self-assembly of hybrid block copolymers containing poly(ethylene glycol) and amphiphilic beta-strand peptide sequences. Biomacromolecules. May-Jun. 2005;6(3):1310-5.
Hartgerink et al., Peptide-amphiphile nanofibers: a versatile scaffold for the preparation of self-assembling materials. Proc Natl Acad Sci U S A. Apr. 16, 2002;99(8):5133-8.
Hartgerink et al., Self-assembly and mineralization of peptide-amphiphile nanofibers. Science. Nov. 23, 2001;294(5547):1684-8.
Iscen et al., Hofmeister Effects on Peptide Amphiphile Nanofiber Self-Assembly. J Phys Chem B. Aug. 15, 2019;123(32):7006-7013.
Israelachvili, Intermolecular and surface forces; 2nd ed.; Academic: London San Diego, 1992. TOC only. 2 pages.
Karakoti et al., PEGylated inorganic nanoparticles. Angew Chem Int Ed Engl. Feb. 25, 2011;50(9):1980-94.
Lee et al., Gel scaffolds of BMP-2-binding peptide amphiphile nanofibers for spinal arthrodesis. Adv Healthc Mater. Jan. 7, 2015;4(1):131-141.
Lee et al., Sulfated glycopeptide nanostructures for multipotent protein activation. Nat Nanotechnol. Aug. 2017;12(8):821-829.
Li et al., Gold nanoparticles with different charge and moiety induce differential cell response on mesenchymal stem cell osteogenesis. Biomaterials. Jun. 2015;54:226-36.
Mayo et al., A recipe for designing water-soluble, beta-sheet-forming peptides. Protein Sci. Jul. 1996;5(7):1301-15.
Monopoli et al., Biomolecular coronas provide the biological identity of nanosized materials. Nat Nanotechnol. Dec. 2012;7(12):779-86.
Moyer et al., pH and amphiphilic structure direct supramolecular behavior in biofunctional assemblies. J Am Chem Soc. Oct. 22, 2014;136(42):14746-52.
Mukherjee et al., Infrared study of the effect of hydration on the amide I band and aggregation properties of helical peptides. J Phys Chem B. May 3, 2007;111(17):4596-602.
Newcomb et al., Cell death versus cell survival instructed by supramolecular cohesion of nanostructures. Nat Commun. 2014;5:3321.
Niece et al., Modification of gelation kinetics in bioactive peptide amphiphiles. Biomaterials. Dec. 2008;29(34):4501-9.
Niece et al., Self-assembly combining two bioactive peptide-amphiphile molecules into nanofibers by electrostatic attraction. J Am Chem Soc. Jun. 18, 2003;125(24):7146-7.
Ortony et al., Internal dynamics of a supramolecular nanofibre. Nat Mater. Aug. 2014;13(8):812-6.
Perinelli et al., PEGylation affects the self-assembling behaviour of amphiphilic octapeptides. Int J Pharm. Nov. 25, 2019;571:118752.
Shrestha et al., Influence of titanium dioxide nanorods with different surface chemistry on the differentiation of rat bone marrow mesenchymal stem cells. J Mater Chem B. Nov. 21, 2016;4(43):6955-6966.
Stuart et al., The use of Nile Red to monitor the aggregation behavior in ternary surfactant-water-organic solvent systems. Journal of Physical Organic Chemistry 2005, 18 (9), 929-934.
Suk et al., PEGylation as a strategy for improving nanoparticle-based drug and gene delivery. Adv Drug Deliv Rev. Apr. 1, 2016;99(Pt A):28-51.
Sur et al., Epitope topography controls bioactivity in supramolecular nanofibers. Biomater Sci. Mar. 2015;3(3):520-32.
Tantakitti et al., Energy landscapes and functions of supramolecular systems. Nat Mater. Apr. 2016;15(4):469-76.
Tew et al., Driving mesenchymal stem cell differentiation from self-assembled monolayers. Rsc Advances 2018, 8 (12), 6551-6564.
Toft et al., Coassembled cytotoxic and pegylated peptide amphiphiles form filamentous nanostructures with potent antitumor activity in models of breast cancer. ACS Nano. Sep. 25, 2012;6(9):7956-65.
Toksoz et al., Electrostatic effects on nanofiber formation of self-assembling peptide amphiphiles. J Colloid Interface Sci. Apr. 1, 2011;356(1):131-7.
Wan et al., Extremely Stable Supramolecular Hydrogels Assembled from Nonionic Peptide Amphiphiles. Langmuir. Aug. 2, 2016;32(30):7512-8.
Wang et al., Gene expression profiling and mechanism study of neural stem cells response to surface chemistry. Regen Biomater. Nov. 2014;1(1):37-47.
Wang et al., Surface charge critically affects tumor penetration and therapeutic efficacy of cancer nanomedicines. Nano Today 2016, 11 (2), 133-144.
Webber et al., Supramolecular PEGylation of biopharmaceuticals. Proc Natl Acad Sci U S A. Dec. 13, 2016;113(50):14189-14194.
Yu et al., Influence of Surface Chemistry on Adhesion and Osteo/Odontogenic Differentiation of Dental Pulp Stem Cells. ACS Biomater Sci Eng. Jun. 12, 2017;3(6):1119-1128.
Zhang et al., A self-assembly pathway to aligned monodomain gels. Nat Mater. Jul. 2010;9(7):594-601.
Zhang et al., Modulating hierarchical self-assembly behavior of a peptide amphiphile/nonionic surfactant mixed system. RSC Advances 2016, 6 (11), 9186-9193.

\* cited by examiner

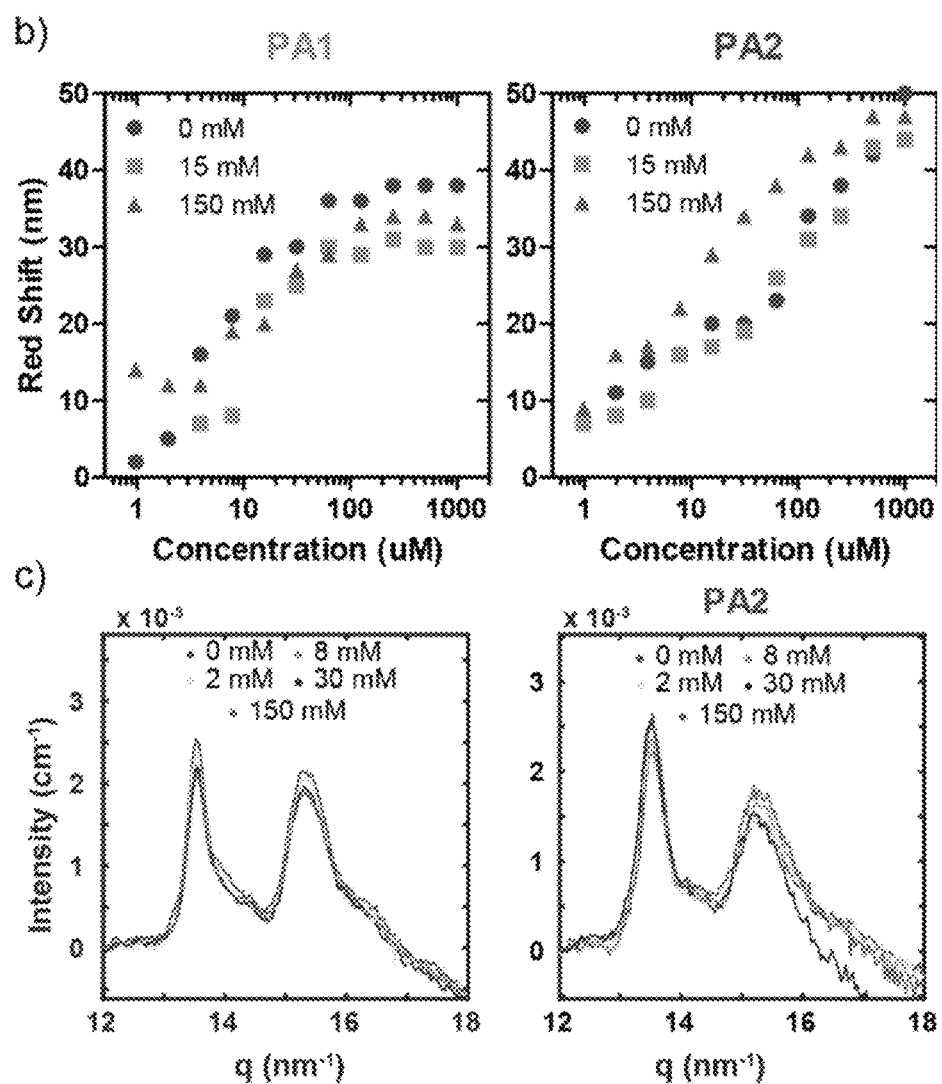
FIG. 2B-C

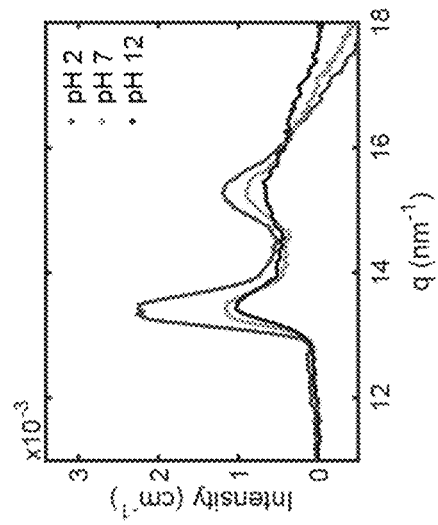
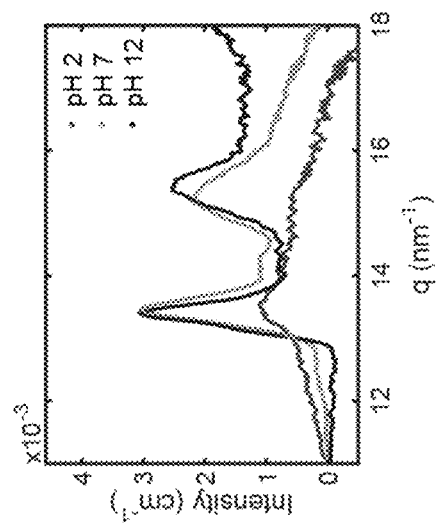
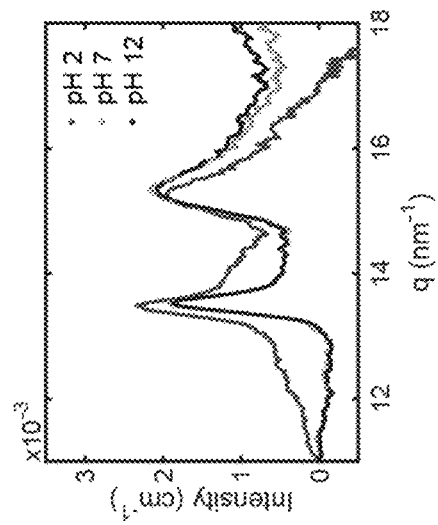
FIG. 2D

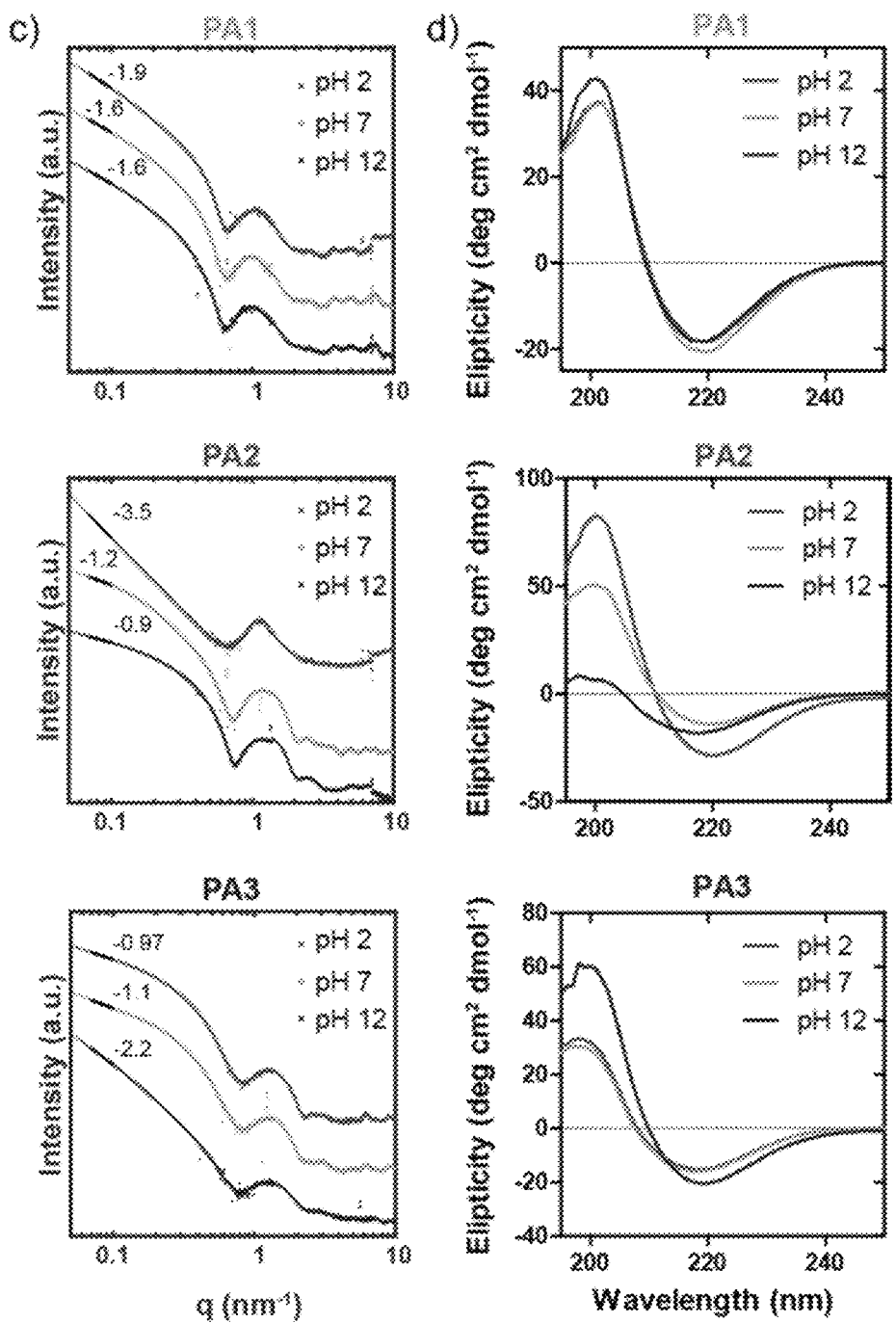
FIG. 7C-D a)
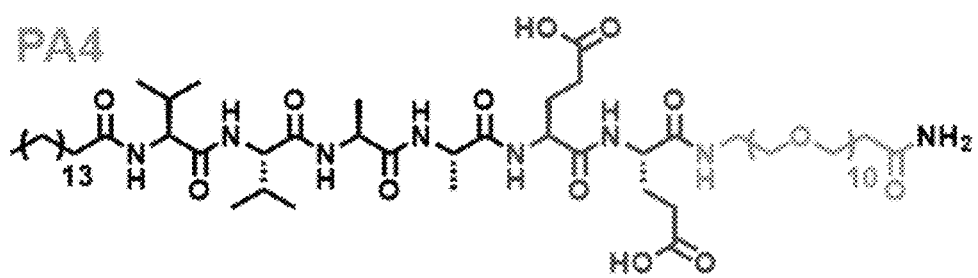
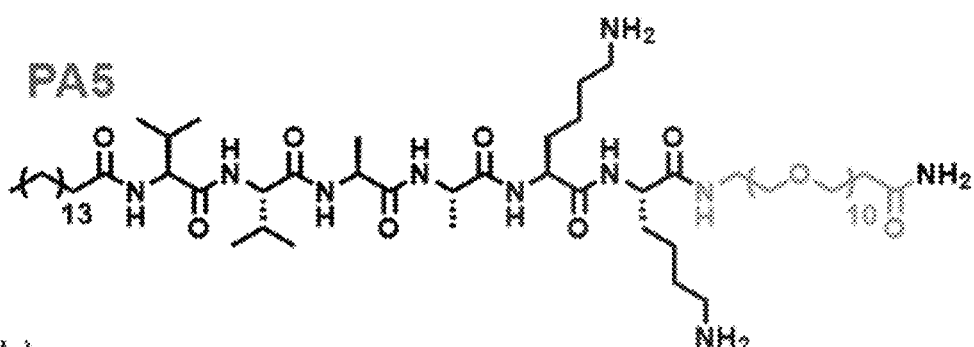
b)
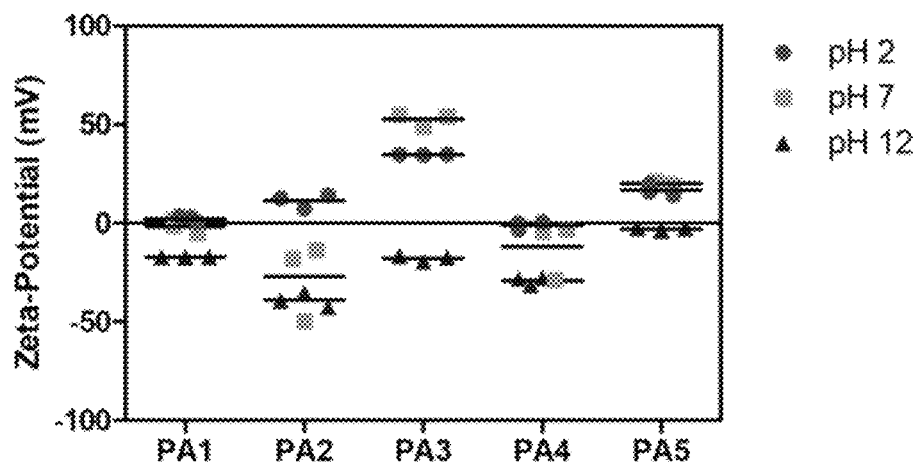
FIG. 8A-B

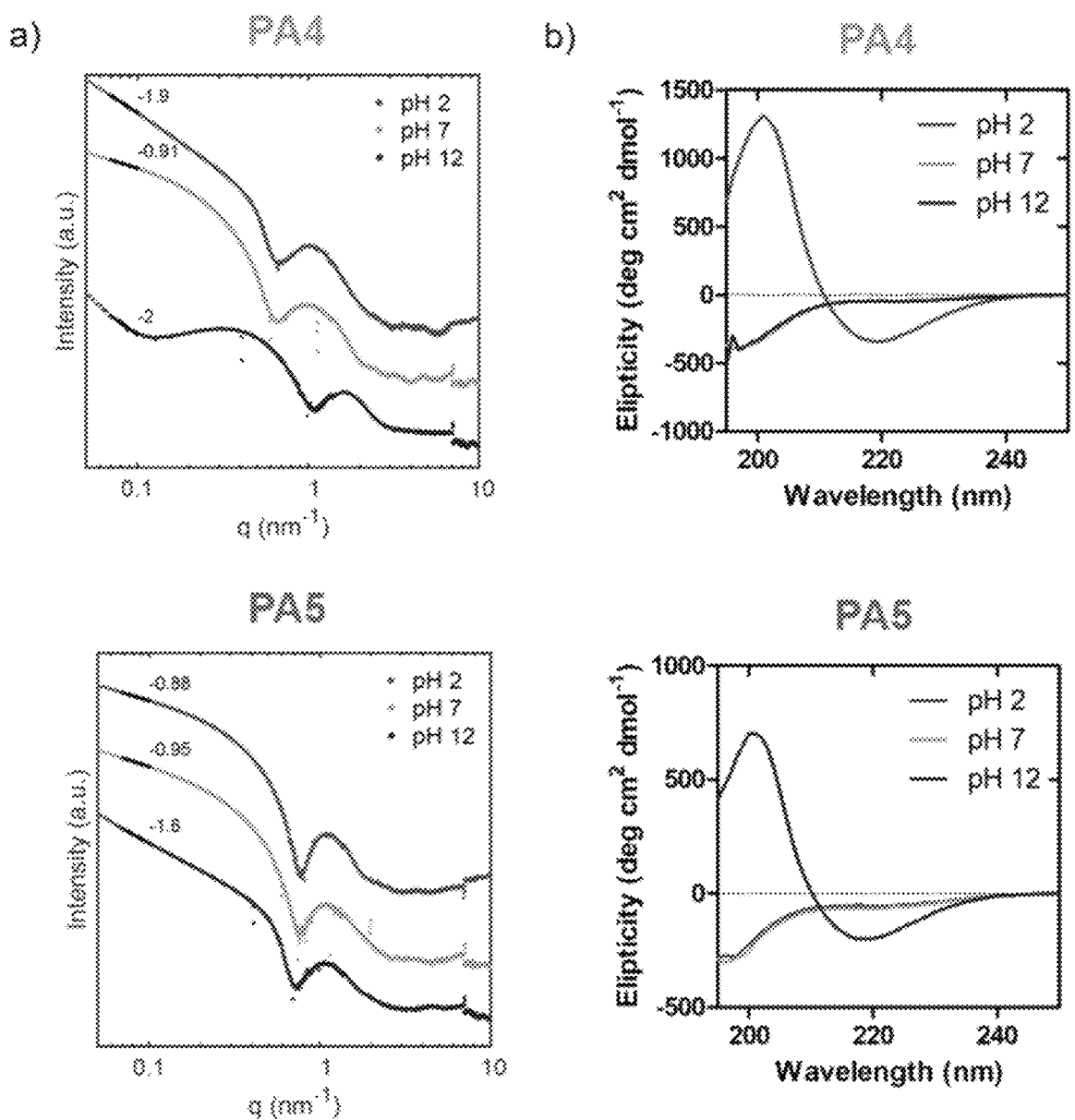
FIG. 9A-B

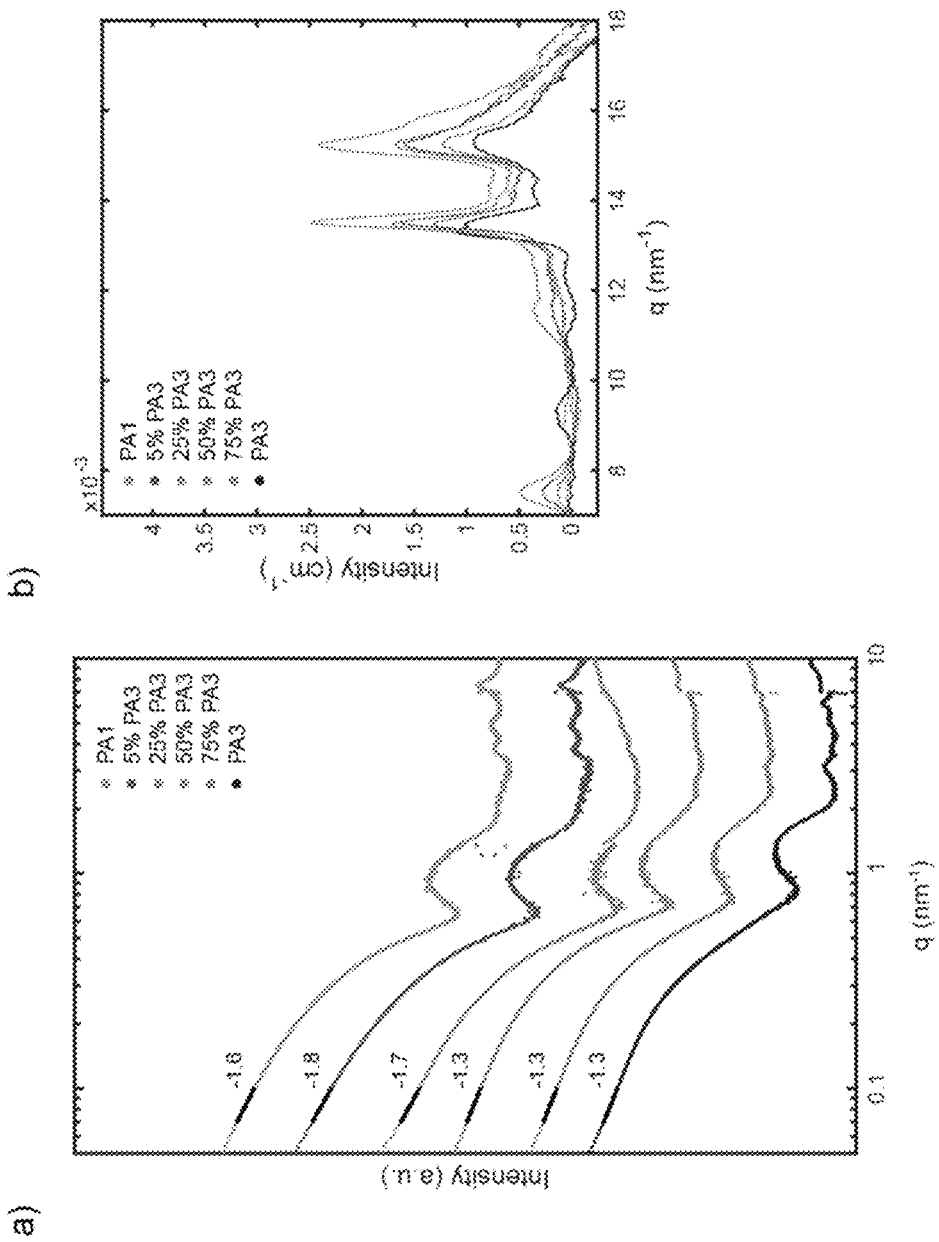
FIG. 11A-B

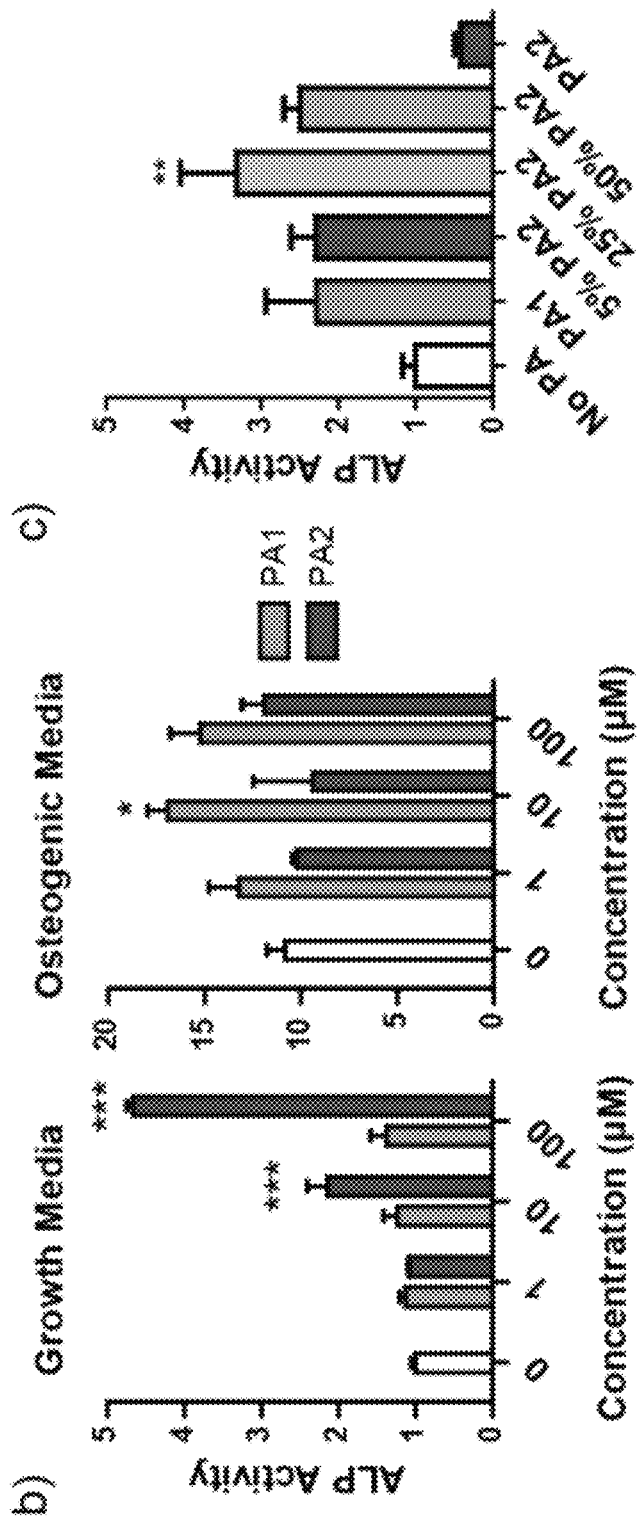
FIG. 12B-C

PEGYLATED PEPTIDE AMPHIPHILE NANOFIBERS AND METHODS OF USE

STATEMENT OF RELATED APPLICATIONS

This application claims priority to U.S. Provisional Patent Application No. 63/051,043, filed Jul. 13, 2020, the entire contents of which are incorporated here by reference.

FIELD

Provided herein are peptide amphiphiles (PAs). In some embodiments, provided herein are PEGylated PAs (e.g. nonionic PAs). In some embodiments, the peptide amphiphiles are assembled into nanofibers. In some embodiments, the nanofibers further comprise a charged peptide amphiphile. The nonionic or charged peptide amphiphile may be bound to a growth factor protein. Further provided herein are methods of use of the peptide amphiphiles and compositions comprising the same, such as for regenerative therapy.

BACKGROUND

Peptide amphiphile (PA) molecules comprising a peptide region conjugated to an alkyl tail are a promising platform for biomedical applications because of their highly tunable self-assembly into dynamic nanostructures in aqueous media. PAs may be used as a delivery platform for various bioactive agents. However, use of such PAs is often hindered by poor bioactivity and/or limited circulation time of the bioactive agent, resulting in a limited cellular response to the agent.

Accordingly, what is needed are novel PA platforms that may be used to enhance the cellular response to bioactive agents, such as growth factor proteins, following delivery to a cell or subject.

SUMMARY

In some aspects, provided herein are peptide amphiphiles. In some embodiments, provided herein are peptide amphiphiles comprising a hydrophobic tail, a structural peptide segment, and a PEG domain.

In some embodiments, the hydrophobic tail comprises an 8-24 carbon alkyl chain ($C_{8-24}$). In some embodiments, the structural peptide segment has a propensity for forming β-sheet conformations. For example, the structural peptide segment may comprise $V_2A_2$ or $V_3A_3$.

In some embodiments, the PEG domain comprises a PEG containing 1-20 repeating ethylene glycol subunits. For example, the PEG may contain 10 repeating ethylene glycol subunits.

In some aspects, provided herein are nanofibers comprising the peptide amphiphiles described herein. In some embodiments, provided herein are nanofibers comprising a nonionic peptide amphiphile and a charged peptide amphiphile. The charged peptide amphiphile may comprise a hydrophobic tail, a structural peptide segment, and a charged peptide segment. In some embodiments, the charged peptide segment is anionic. For example, the charged peptide segment may comprise $E_{2-4}$.

In some embodiments, the nanofiber further comprises at least one growth factor protein.

The growth factor protein may be bound to the charged peptide amphiphile. The growth factor protein may be bound to the nonionic peptide amphiphile.

In some aspects, provided herein are compositions comprising a nanofiber as described herein. The compositions may be provided to a cell or a subject. For example, the compositions may be provided to a subject to promote regeneration of one or more damaged bones or tissues in the subject.

BRIEF DESCRIPTION OF THE DRAWINGS

FIG. 1A-J show exemplary nonionic (e.g. PEGylated) peptide amphiphiles described herein. These molecules necessarily include 3 chemical domains, and optionally include a fourth bioactive domain. The necessary domains include a hydrophobic domain (black), a peptide domain (red), and a PEG domain (blue). In water, the molecules are found to self-assemble with the PEG groups on the surface of the assembly and the alkyl chains collapsed within the assembly. A library of these peptides have been produced with varying alkyl tail (8-16) and PEG lengths (6-20). FIGS. 1A, 1B, 1C, 1D, and 1E show exemplary nonionic peptide amphiphiles described herein. These generally form fiber or rod structures depending on the size of each domain. The molecules are synthesized by fmoc solid phase peptide synthesis using a commercially available PEG amino acid group. They can be purified by HPLC in either acidic or basic conditions.

As shown in FIGS. 1F, 1G, 1H, and 1I, a bioactive peptide domain can be added to the PA molecule (green). This can be done at the C-terminus or the N-terminus. Addition at the N-terminus requires producing a "reverse PA" where the alkyl tail is attached to a lysine sidechain at the C-terminus followed by addition of the peptide groups in reverse order. This system has been used to display the adhesive epitope RGDS (FIG. 1H forward) and the TGFβ-1 binding epitope HSNGLPL (FIG. 1F, FIG. 1G reverse). This system is used to produce PA molecules that are incompatible with basic purification by substituting charged amino acids for a PEGylated group.

FIG. 2. (FIG. 2B) Redshift of peak Nile red fluorescence as a function of PA1 and PA2 concentration at in buffers of 0 mM NaCl, 15 mM NaCl, and 150 mM NaCl. (FIG. 2C) Intensity of x-ray scattering by PA1 and PA2 solutions in buffers of 0 mM, 2 mM, 8 mM, 30 mM, and 150 mM NaCl. (FIG. 2D) wide-angle x-ray scattering patterns of PA assemblies. Self-assembly of PEG-PA molecules (PA1, left panel) is largely pH independent, with minimal structural changes in acidic and basic pH. In charged PA systems (PA2, middle panel and PA3, right panel), pH changes had a significant effect on self-assembled structure.

FIG. 6.

FIG. 7. (FIG. 7C) Small-angle x-ray scattering intensity as a function of the wave vector for PA1, PA2, and PA3 solutions at $pH_2$, pH 7, and pH 12. (FIG. 7D) CD as a function of wavelength for PA1, PA2, and PA3 solutions at $pH_2$, pH 7, and pH 12.

FIG. 8. (FIG. 8A) Structures of anionic, PEG-appended PA4 and cationic, PEG-appended PA5. (FIG. 8B) Zeta-potential measurements for all PA molecules tested.

FIG. 9. (FIG. 9A) Small-angle x-ray scattering intensity as a function of the wave vector for PA4 and PA5 solutions at $pH_2$, pH 7, and pH 12. (FIG. 9B) Circular dichroism as a function of wavelength for PA4 and PA5 solutions at $pH_2$, pH 7, and pH 12 in 30 mM NaCl.

FIG. 10.

FIG. 11. (FIG. 11A) SAXS intensities of co-assembled systems of PA1 and PA3 as a function of the wave vector. (FIG. 11B) WAXS intensities of the co-assembled systems of PA1 and PA3 as a function of the wave vector.

FIG. 12. (FIG. 12B) ALP activity normalized to DNA content as a function of PA concentration for human MSCs cultured in growth media and in osteogenic media for 7 days;

significance calculated relative to no PA control in growth media. (FIG. 12C) ALP activity normalized to DNA content for PA1 and PA2 co-assemblies cultured in osteogenic media for 14 days; significance calculated relative to no PA control. (*, $p<0.05$; , $p<0.01$; *, $p<0.001$)

Definitions

Figures 1A, 1B, 1C, 1D, 1E:
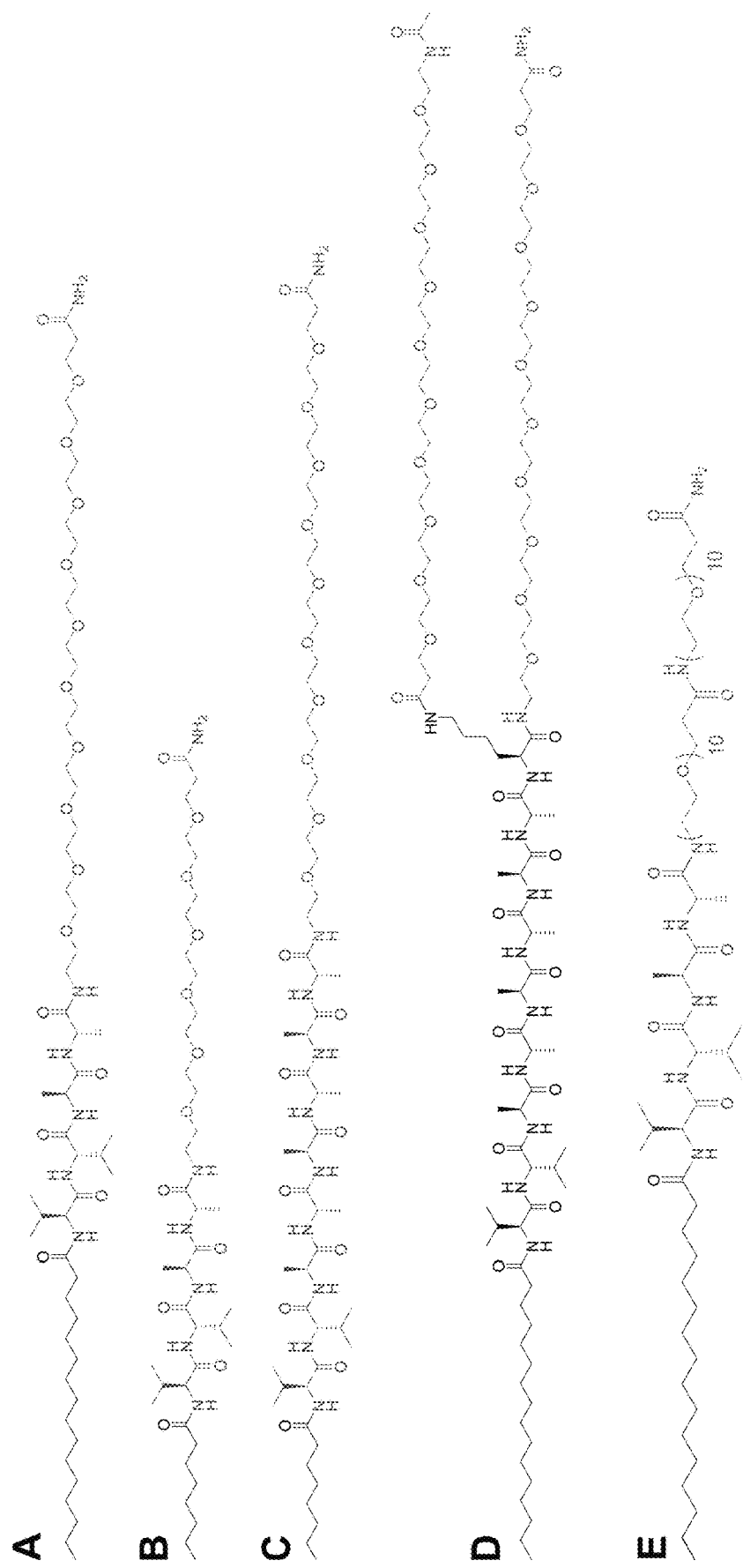
Figures 1F, 1G:
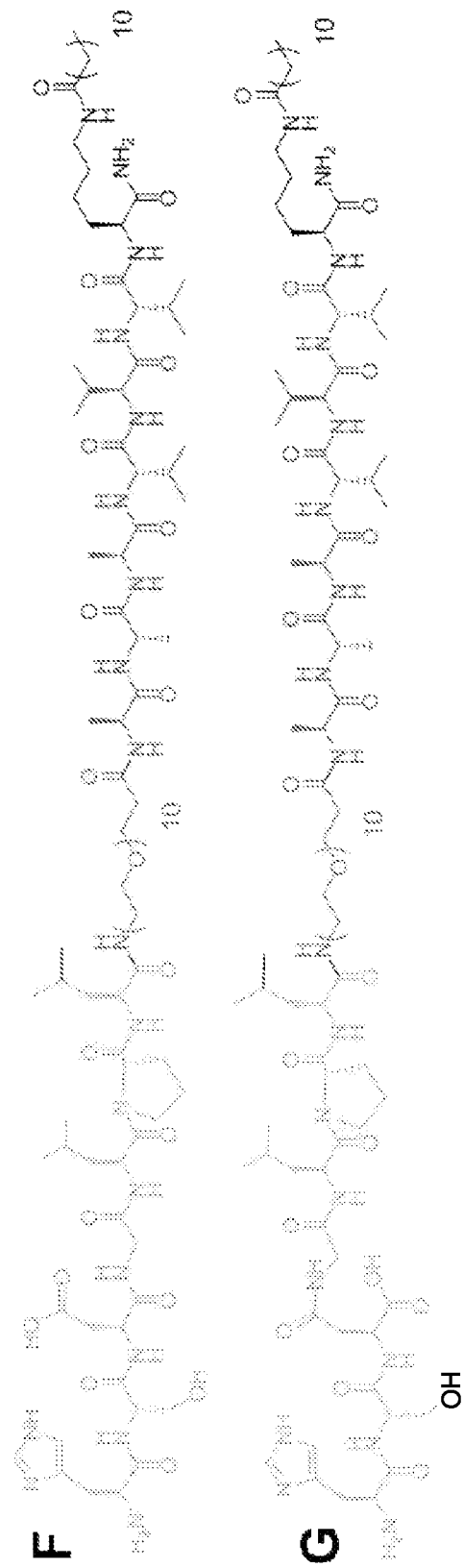

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a peptide amphiphile" is a reference to one or more peptide amphiphiles and equivalents thereof known to those skilled in the art, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method.

Many embodiments herein are described using open "comprising" language. Such embodiments encompass multiple closed "consisting of" and/or "consisting essentially of" embodiments, which may alternatively be claimed or described using such language.

The term "amino acid" refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids include, but are not limited to, azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), N-alkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("OctG"), ornithine ("Orn"), pentylglycine ("pG" or "PGly"), pipecolic acid, thioproline ("ThioP" or "tPro"), homoLysine ("hLys"), and homoArginine ("hArg").

The term "amino acid analog" refers to a natural or unnatural amino acid where one or more of the C-terminal carboxy group, the N-terminal amino group and side-chain bioactive group has been chemically blocked, reversibly or irreversibly, or otherwise modified to another bioactive group. For example, aspartic acid-(beta-methyl ester) is an amino acid analog of aspartic acid; N-ethylglycine is an amino acid analog of glycine; or alanine carboxamide is an amino acid analog of alanine. Other amino acid analogs include methionine sulfoxide, methionine sulfone, S-(carboxymethyl)-cysteine, S-(carboxymethyl)-cysteine sulfoxide and S-(carboxymethyl)-cysteine sulfone.

As used herein, the term "peptide" refers an oligomer to short polymer of amino acids linked together by peptide bonds. In contrast to other amino acid polymers (e.g., proteins, polypeptides, etc.), peptides are of about 50 amino acids or less in length. A peptide may comprise natural amino acids, non-natural amino acids, amino acid analogs, and/or modified amino acids. A peptide may be a subsequence of naturally occurring protein or a non-natural (artificial) sequence.

As used herein, the term "artificial" refers to compositions and systems that are designed or prepared by man, and are not naturally occurring. For example, an artificial peptide, peptoid, or nucleic acid is one comprising a non-natural sequence (e.g., a peptide without 100% identity with a naturally-occurring protein or a fragment thereof).

As used herein, a "conservative" amino acid substitution refers to the substitution of an amino acid in a peptide or polypeptide with another amino acid having similar chemical properties, such as size or charge. For purposes of the present disclosure, each of the following eight groups contains amino acids that are conservative substitutions for one another:

1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M), and Valine (V);
6) Phenylalanine (F), Tyrosine (Y), and Tryptophan (W);
7) Serine (S) and Threonine (T); and
8) Cysteine (C) and Methionine (M).

Naturally occurring residues may be divided into classes based on common side chain properties, for example: polar positive (or basic) (histidine (H), lysine (K), and arginine (R)); polar negative (or acidic) (aspartic acid (D), glutamic acid (E)); polar neutral (serine (S), threonine (T), asparagine (N), glutamine (Q)); non-polar aliphatic (alanine (A), valine (V), leucine (L), isoleucine (I), methionine (M)); non-polar aromatic (phenylalanine (F), tyrosine (Y), tryptophan (W)); proline and glycine; and cysteine. As used herein, a "semi-conservative" amino acid substitution refers to the substitution of an amino acid in a peptide or polypeptide with another amino acid within the same class.

In some embodiments, unless otherwise specified, a conservative or semi-conservative amino acid substitution may also encompass non-naturally occurring amino acid residues that have similar chemical properties to the natural residue. These non-natural residues are typically incorporated by chemical peptide synthesis rather than by synthesis in biological systems. These include, but are not limited to, peptidomimetics and other reversed or inverted forms of amino acid moieties. Embodiments herein may, in some embodiments, be limited to natural amino acids, non-natural amino acids, and/or amino acid analogs.

Non-conservative substitutions may involve the exchange of a member of one class for a member from another class.

As used herein, the term "sequence identity" refers to the degree of which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) differ only by conservative and/or semi-conservative amino acid substitutions. The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

Any polypeptides described herein as having a particular percent sequence identity or similarity (e.g., at least 70%) with a reference sequence ID number, may also be expressed as having a maximum number of substitutions (or terminal deletions) with respect to that reference sequence. For example, a sequence having at least Y % sequence identity (e.g., 90%) with SEQ ID NO:Z (e.g., 100 amino acids) may have up to X substitutions (e.g., 10) relative to SEQ ID NO:Z, and may therefore also be expressed as "having X (e.g., 10) or fewer substitutions relative to SEQ ID NO:Z."

As used herein, the term "nanofiber" refers to an elongated or threadlike filament (e.g., having a significantly greater length dimension that width or diameter) with a diameter typically less than 100 nanometers.

As used herein, the term "scaffold" refers to a material capable of supporting growth and differentiation of a cell.

As used herein, the term "supramolecular" (e.g., "supramolecular complex," "supramolecular interactions," "supramolecular fiber," "supramolecular polymer," etc.) refers to the non-covalent interactions between molecules (e.g., polymers, macromolecules, etc.) and the multicomponent assemblies, complexes, systems, and/or fibers that form as a result.

As used herein, the terms "self-assemble" and "self-assembly" refer to formation of a discrete, non-random, aggregate structure from component parts; said assembly occurring spontaneously through random movements of the components (e.g. molecules) due only to the inherent chemical or structural properties and attractive forces of those components.

As used herein, the term "peptide amphiphile" refers to a molecule that, at a minimum, includes a lipophilic (hydrophobic) segment and a structural peptide segment. The term "peptide amphiphile" includes "nonionic peptide amphiphiles" and "charged peptide amphiphiles". A "nonionic peptide amphiphile" comprises a hydrophobic segment, a structural peptide segment, and a PEG domain. A "charged peptide amphiphile" comprises a hydrophobic segment, a structural peptide segment, and a charged peptide segment. The charged peptide amphiphile may express a net charge at physiological pH, either a net positive or negative net charge, or may be zwitterionic (i.e., carrying both positive and negative charges).

As used herein and in the appended claims, the term "lipophilic moiety" or "hydrophobic moiety" refers to the moiety (e.g., an acyl, ether, sulfonamide, or phosphodiester moiety) disposed on one terminus (e.g., C-terminus, N-terminus) of the peptide amphiphile, and may be herein and elsewhere referred to as the lipophilic or hydrophobic segment or component. The hydrophobic segment should be of a sufficient length to provide amphiphilic behavior and aggregate (or nanosphere or nanofiber) formation in water or another polar solvent system. Accordingly, in the context of the embodiments described herein, the hydrophobic component preferably comprises a single, linear acyl chain of the formula: $C_{n-1}H_{2n-1}C(O)$— where n=2-25. In some embodiments, a linear acyl chain is the lipophilic group (saturated or unsaturated carbons), palmitic acid. However, other lipophilic groups may be used in place of the acyl chain such as steroids, phospholipids and fluorocarbons. As used interchangeably herein, the terms "structural peptide" or "structural peptide segment" refer to a portion of a peptide amphiphile, typically disposed between the hydrophobic segment and the charged peptide segment or between the hydrophobic segment and the PEG domain. The structural peptide is generally composed of three to ten amino acid residues with non-polar, uncharged side chains (e.g., His (H), Val (V), Ile (I), Leu (L), Ala (A), Phe (F)) selected for their propensity to form hydrogen bonds or other stabilizing interactions (e.g., hydrophobic interactions, van der Waals' interactions, etc.) with structural peptide segments of adjacent structural peptide segments. In some embodiments, nanofibers of peptide amphiphiles having structural peptide segments display linear or 2D structure when examined by microscopy and/or a-helix and/or (3-sheet character when examined by circular dichroism (CD). As used herein, the term "beta (β)-sheet-forming peptide segment" refers to a structural peptide segment that has a propensity to display (3-sheet-like character (e.g., when analyzed by CD). In some embodiments, amino acids in a beta (β)-sheet-forming peptide segment are selected for their propensity to form a beta-sheet secondary structure. Examples of suitable amino acid residues selected from the twenty naturally occurring amino acids include Met (M), Val (V), Ile (I), Cys (C), Tyr (Y), Phe (F), Gln (Q), Leu (L), Thr (T), Ala (A), and Gly (G) (listed in order of their propensity to form beta sheets). However, non-naturally occurring amino acids of similar beta-sheet forming propensity may also be used. Peptide segments capable of interacting to form beta sheets and/or with a propensity to form beta sheets are understood (See, e.g., Mayo et al. Protein Science (1996), 5:1301-1315; herein incorporated by reference in its entirety).

As used herein, the term "charged peptide segment" refers to a portion of a peptide amphiphile that is rich (e.g., >50%, >75%, etc.) in charged amino acid residues, or amino acid residue that have a net positive or negative charge under physiologic conditions. A charged peptide segment may be acidic (e.g., negatively charged/anionic), basic (e.g., positively charged/cationic), or zwitterionic (e.g., having both acidic and basic residues). In particular embodiments, the peptide segment is negatively charged.

As used herein, the terms "carboxy-rich peptide segment," "acidic peptide segment," and "negatively-charged peptide segment" refer to a peptide sequence of a peptide amphiphile that comprises one or more amino acid residues that have side chains displaying carboxylic acid side chains (e.g., Glu (E), Asp (D), or non-natural amino acids). A carboxy-rich peptide segment may optionally contain one or more additional (e.g., non-acidic) amino acid residues. Non-natural amino acid residues, or peptidomimetics with acidic side chains could be used, as will be evident to one ordinarily skilled in the art. There may be from about 2 to about 7 amino acids, and or about 3 or 4 amino acids in this segment.

As used herein, the terms "amino-rich peptide segment", "basic peptide segment," and "positively-charged peptide segment" refer to a peptide sequence of a peptide amphiphile that comprises one or more amino acid residues that have side chains displaying positively-charged acid side chains (e.g., Arg (R), Lys (K), His (H), or non-natural amino acids, or peptidomimetics). A basic peptide segment may optionally contain one or more additional (e.g., non-basic) amino acid residues. Non-natural amino acid residues with basic side chains could be used, as will be evident to one ordinarily skilled in the art. There may be from about 2 to about 7 amino acids, and or about 3 or 4 amino acids in this segment.

As used herein, the term "biocompatible" refers to materials and agents that are not toxic to cells or organisms. In some embodiments, a substance is considered to be "biocompatible" if its addition to cells in vitro results in less than or equal to approximately 10% cell death, usually less than 5%, more usually less than 1%.

As used herein, "biodegradable" as used to describe the polymers, hydrogels, and/or wound dressings herein refers to compositions degraded or otherwise "broken down" under exposure to physiological conditions. In some embodiments, a biodegradable substance is a broken down by cellular machinery, enzymatic degradation, chemical processes, hydrolysis, etc. In some embodiments, a wound dressing or coating comprises hydrolyzable ester linkages that provide the biodegradability.

As used herein, the term "growth factor" or "growth factor protein" are used in the broadest sense and refer to any naturally occurring substance capable of stimulating cellular growth, proliferation, healing, or cellular differentiation. Typically, "growth factor" as referred to herein is a protein.

As used herein, the term "PEG domain" refers to a domain comprising at least one polyethlene glycol (PEG) or derivative thereof. The term "polyethylene glycol" or "PEG" as used interchangeably herein refers to a polyether compound typically denoted by the structure $H-(O-CH_2-CH_2)_n-OH$. As denoted by the structure, a PEG may comprise a number of repeating ethylene glycol ($O-CH_2-CH_2$) subunits, denoted by "n". A single ethylene glycol subunit of PEG has a molecular weight of approximately 44 Daltons. Therefore, the molecular weight of the PEG polymer depends on the number (n). In some embodiments, the term PEG domain may refer to a domain comprising at least one PEG containing 1-20 repeating ethylene glycol subunits (e.g. $H-(O-CH_2-CH_2)_{1-20}-OH$.). For example, the PEG may contain 10 repeating ethylene glycol subunits (e.g. H—(O—CH$_2$—CH$_2$)$_{10}$—OH). The term "PEG" also includes PEG derivatives, or PEGs coupled to other moieties.

As used herein, the phrase "physiological conditions" relates to the range of chemical (e.g., pH, ionic strength) and biochemical (e.g., enzyme concentrations) conditions likely to be encountered in the intracellular and extracellular fluids of tissues. For most tissues, the physiological pH ranges from about 7.0 to 7.4.

As used herein, the terms "treat," "treatment," and "treating" refer to reducing the amount or severity of a particular condition, disease state or symptoms thereof, in a subject presently experiencing or afflicted with the condition or disease state. The terms do not necessarily indicate complete treatment (e.g., total elimination of the condition, disease, or symptoms thereof). "Treatment," encompasses any administration or application of a therapeutic or technique for a disease (e.g., in a mammal, including a human), and includes inhibiting the disease, arresting its development, relieving the disease, causing regression, or restoring or repairing a lost, missing, or defective function; or stimulating an inefficient process.

As used herein, the terms "prevent," "prevention," and "preventing" refer to reducing the likelihood of a particular condition or disease state from occurring in a subject not presently experiencing or afflicted with the condition or disease state. The terms do not necessarily indicate complete or absolute prevention. For example, "prevention" refers to reducing the likelihood of a condition or disease state occurring in a subject not presently experiencing or diagnosed with the condition or disease state. In order to "prevent" a condition or disease state, a composition or method need only reduce the likelihood of the condition or disease state, not completely block any possibility thereof. "Prevention," encompasses any administration or application of a therapeutic or technique to reduce the likelihood of a disease developing (e.g., in a mammal, including a human). Such a likelihood may be assessed for a population or for an individual.

As used herein, the terms "co-administration" and "co-administering" refer to the administration of at least two agent(s) or therapies to a subject (e.g., a PA nanofiber and one or more therapeutic agents). In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

DETAILED DESCRIPTION

PA molecules generally contain charged amino acid residues for solubility, constituting the hydrophilic domain of the amphiphile. These can include acid residues which are deprotonated at neutral pH or basic residues protonated at neutral pH. In addition to ionically charged amino acids, a widely used subclass of PA molecules includes a peptide sequence designed to promote hydrogen bonding among molecules, which programs self-assembly of high-aspect ratio, one-dimensional nanostructures. Self-assembly of these molecules produces nanostructures with a high density of surface charge and screening of these charges, in part, determines how the structures assemble. The charged groups in these assemblies determine many properties of the nanostructures including peptide bioactivity, cytocompatibility, biodistribution, and gel formation. However, how the effect of tuning or eliminating completely ionic charge within PA systems affects intermolecular interactions and the resultant biological response of cells to the assembly these assemblies remains unknown.

In some aspects, provided herein are peptide amphiphiles (PAs) and compositions comprising the same. In some aspects, provided herein are nanofibers comprising the peptide amphiphiles described herein. In some embodiments, provided herein are methods of use of the PAs and nanofibers disclosed herein. The term "peptide amphiphile" as used herein is inclusive of both charged and nonionic (i.e. PEGylated) peptide amphiphiles.

In some embodiments, provided herein are nonionic PAs comprising a PEG domain (i.e., PEGylated PAs). In some embodiments, provided herein are nanofibers comprising the nonionic (i.e. PEGylated) PAs described herein. Further provided herein are methods of use of the nonionic PAs and nanofibers disclosed herein.

In some embodiments, provided herein are charged PAs comprising a charged peptide domain. In some embodiments, provided herein are nanofibers comprising the charged PAs described herein, along with methods of using the same.

In some embodiments, the peptide amphiphile molecules and compositions of the embodiments described herein are synthesized using preparatory techniques well-known to those skilled in the art, preferably, by standard solid-phase peptide synthesis, with the addition of a fatty acid in place of a standard amino acid at the N-terminus (or C-terminus) of the peptide, in order to create the lipophilic segment (although in some embodiments, alignment of nanofibers is performed via techniques not previously disclosed or used in the art (e.g., extrusion through a mesh screen). Synthesis typically starts from the C-terminus, to which amino acids are sequentially added using either a Rink amide resin (resulting in an —NH$_2$ group at the C-terminus of the peptide after cleavage from the resin), or a Wang resin (resulting in an —OH group at the C-terminus). Accordingly, some embodiments described herein encompass peptide amphiphiles having a C-terminal moiety that may be selected from the group consisting of —H, —OH, —COOH, —CONH$_2$, and —NH$_2$.

In some embodiments, peptide amphiphiles comprise a hydrophobic segment (i.e. a hydrophobic tail) linked to a peptide. In some embodiments, the peptide comprises a structual peptide segment. In some embodiments, the structural peptide segment is a hydrogen-bond-forming segment, or beta-sheet-forming segment.

In some embodiments, the peptide amphiphile further comprises linker or spacer segments for adding solubility, flexibility, distance between segments, etc. In some embodiments, peptide amphiphiles comprise a spacer segment (e.g., peptide and/or non-peptide spacer) at the opposite terminus of the peptide from the hydrophobic segment. In some embodiments, the spacer segment comprises peptide and/or non-peptide elements. In some embodiments, the spacer segment comprises one or more bioactive groups (e.g., alkene, alkyne, azide, thiol, etc.). In some embodiments, various segments may be connected by linker segments (e.g., peptide or non-peptide (e.g., alkyl, OEG, PEG, etc.) linkers).

The lipophilic or hydrophobic segment is typically incorporated at the N- or C-terminus of the peptide after the last amino acid coupling, and is composed of a fatty acid or other acid that is linked to the N- or C-terminal amino acid through an acyl bond. In aqueous solutions, PA molecules may self-assemble (e.g., into cylindrical micelles (a.k.a., nanofibers)) to bury the lipophilic segment in their core. In some embodiments, nonionic PAs and charged PAs may coassemble into a nanofiber. In some embodiments, the structural peptide undergoes intermolecular hydrogen bonding to form beta sheets that orient parallel to the long axis of the micelle.

In some embodiments, compositions described herein comprise PA building blocks that in turn comprise a hydrophobic segment and a peptide segment. In certain embodiments, a hydrophobic (e.g., hydrocarbon and/or alkyl/alkenyl/alkynyl tail, or steroid such as cholesterol) segment of sufficient length (e.g., 2 carbons, 3 carbons, 4 carbons, 5 carbons, 6 carbons, 7 carbons, 8 carbons, 9 carbons, 10 carbons, 11 carbons, 12 carbons, 13 carbons, 14 carbons, 15 carbons, 16 carbons, 17 carbons, 18 carbons, 19 carbons, 20 carbons, 21 carbons, 22 carbons, 23 carbons, 24 carbons, 25 carbons, 26 carbons, 27 carbons, 28 carbons, 29 carbons, 30 carbons or more, or any ranges there between.) is covalently coupled to peptide segment (e.g., a peptide comprising a segment having a preference for beta-strand conformations or other supramolecular interactions) to yield a peptide amphiphile molecule. In some embodiments, a plurality of such PAs will self-assemble in water (or aqueous solution) into a nanostructure (e.g., nanofiber). In various embodiments, the relative lengths of the peptide segment and hydrophobic segment result in differing PA molecular shape and nanostructural architecture. For example, a broader peptide segment and narrower hydrophobic segment results in a generally conical molecular shape that has an effect on the assembly of PAs (See, e.g., J. N. Israelachvili Intermolecular and surface forces; 2nd ed.; Academic: London San Diego, 1992; herein incorporated by reference in its entirety). Other molecular shapes have similar effects on assembly and nanostructural architecture.

In some embodiments, to induce self-assembly of an aqueous solution of peptide amphiphiles, the pH of the solution may be changed (raised or lowered) or multivalent ions, such as calcium, or charged polymers or other macromolecules may be added to the solution.

In some embodiments, the hydrophobic segment is a non-peptide segment (e.g., alkyl/alkenyl/alkynyl group). In some embodiments, the hydrophobic segment comprises an alkyl chain (e.g., saturated) of 4-25 carbons (e.g., 4, 5, 6, 7, 8, 9, 10, 11, 12, 13, 14, 15, 16, 17, 18, 19, 20, 21, 22, 23, 24, 25), fluorinated segments, fluorinated alkyl tails, heterocyclic rings, aromatic segments, pi-conjugated segments, cycloalkyls, oligothiophenes etc. In some embodiments, the hydrophobic segment comprises an acyl/ether chain (e.g., saturated) of 2-30 carbons (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30).

In some embodiments, PAs comprise one or more peptide segments. Peptide segments may comprise natural amino acids, modified amino acids, unnatural amino acids, amino acid analogs, peptidomimetics, or combinations thereof. In some embodiments, peptide segment comprise at least 50% sequence identity or similarity (e.g., conservative or semi-conservative) to one or more of the peptide sequences described herein.

In some embodiments, peptide amphiphiles comprises a structural peptide segment. In some embodiments, the structural peptide segment is a beta-sheet-forming segment. In some embodiments, the structural peptide segment displays weak hydrogen bonding and has the propensity to form random coil structures rather than rigid beta-sheet conformations. In some embodiments, the structural peptide segment is rich in one or more of H, I, L, F, V, G, and A residues. In some embodiments, the structural peptide segment comprises an alanine- and valine-rich peptide segment (e.g., $A_3V_3$, $V_2A_4$, $V_3A_3$, $V_2A_2$, $V_4A_2$) or other combinations of V and A residues, etc.). In some embodiments, the structural peptide segment comprises 4 or more consecutive A and/or V residues, or conservative or semi-conservative substitutions thereto. In some embodiments, the structural peptide segment comprises $V_2A_2$ or $V_3A_3$.

In some embodiments, nonionic peptide amphiphiles comprise a PEG domain. A PEG domain refers to a domain comprising at least one polyethylene glycol (PEG) or derivative thereof. PEG refers to a polyether compound typically denoted by the structure $H-(O-CH_2-CH_2)_n-OH$. As denoted by the structure, a PEG may comprise a number of repeating ethylene glycol ($O-CH_2-CH_2$) subunits, denoted by "n". In some embodiments, the PEG domain comprises at least one PEG containing 1-20 repeating ethylene glycol subunits (e.g. $H-(O-CH_2-CH_2)_{1-20}-OH$.). For example, the PEG may contain 10 repeating ethylene glycol subunits (e.g. $H-(O-CH_2-CH_2)_{10}-OH$). The PEG may be conjugated to other suitable moieties to impart the desired characteristics to the PA described herein.

For example, nonionic peptide amphiphiles may comprise a PEG domain comprising any suitable PEG. In some embodiments, the PEG contains 1-20 repeating ethylene glycol subunits. For example, the PEG may comprise 1, 2, 3, 4, 5, 6, 7, 8, 9, 10, 11, 12, 13, 14, 15, 16, 17, 18, 19, or 20 repeating ethylene glycol subunits. In particular embodiments, the PEG comprises 10 repeating ethylene glycol subunits. In some embodiments, the PEG domain is attached to the structural peptide segment.

In some embodiments, peptide amphiphiles comprise a spacer or linker segment. In some embodiments, the spacer or linker segment is located at the opposite terminus of the peptide from the hydrophobic segment. In some embodiments, the linker segment is a non-peptide linker. In some embodiments, the spacer or linker segment provides the attachment site for a bioactive group. In some embodiments, the spacer or linker segment provides a reactive group (e.g., alkene, alkyne, azide, thiol, maleimide etc.) for functionalization of the PA. In some embodiments, the spacer or linker is a substantially linear chain of $CH_2$, O, $(CH_2)_2O$, $(CH_2)_2$, NH, and C=O groups (e.g., $CH_2(O(CH_2)_2)_2NH$, $CH_2(O(CH_2)_2)_2NHCO(CH_2)_2CCH$, etc.). In some embodiments, a spacer or linker further comprises additional bioactive groups, substituents, branches, etc. In some embodiments, the linker segment is a single glycine (G) residue. In some embodiments, the linker segment is a tripeptide linker (e.g. GSG).

Suitable peptide amphiphiles for use in the materials herein, as well as methods of preparation of PAs and related materials, amino acid sequences for use in PAs, and materials that find use with PAs, are described in the following patents: U.S. Pat. Nos. 9,044,514; 9,040,626; 9,011,914; 8,772,228; 8,748,569 8,580,923; 8,546,338; 8,512,693;

8,450,271; 8,236,800; 8,138,140; 8,124,583; 8,114,835; 8,114,834; 8,080,262; 8,076,295; 8,063,014; 7,851,445; 7,838,491; 7,745,708; 7,683,025; 7,554,021; 7,544,661; 7,534,761; 7,491,690; 7,452,679; 7,371,719; 7,030,167; all of which are herein incorporated by reference in their entireties.

The characteristics (e.g., shape, rigidity, hydrophilicity, etc.) of a PA supramolecular structure depend upon the identity of the components of a peptide amphiphile (e.g., lipophilic segment, acidic segment, structural peptide segment, targeting moiety, etc.). For example, nanofibers, nanospheres, intermediate shapes, and other supramolecular structures are achieved by adjusting the identity of the PA component parts. In some embodiments, characteristics of supramolecular nanostructures of PAs are altered by post-assembly manipulation (e.g., heating/cooling, stretching, etc.).

In some embodiments, a nonionic peptide amphiphile comprises: (a) a hydrophobic tail comprising an alkyl chain of 8-24 carbons; (b) a structural peptide segment (e.g., comprising $V_2A_2$); and (c) a PEG domain (e.g., a PEG comprising 10 repeating ethylene glycol subunits). In some embodiments, any PAs within the scope described herein, comprising the components described herein, or within the skill of one in the field, may find use herein.

In some embodiments, a nonionic peptide amphiphile comprises (e.g., from C-terminus to N-terminus or from N-terminus to C-terminus): PEG domain (e.g. a PEG comprising 10 repeating ethylene glycol subunits)—structural peptide segment (e.g., $V_2A_2$)—hydrophobic tail (e.g., comprising an alkyl chain of 8-24 carbons).

In some embodiments, a PA further comprises an attachment segment or residue (e.g., K) for attachment of one or more segments of the PA to another segment. For example, the PA may further comprise a residue for attachment the hydrophobic tail to the peptide potion of the PA. In some embodiments, the hydrophobic tail is attached to a lysine side chain.

Exemplary nonionic (e.g. PEGylated) PAs are shown in FIG. 1A-J.

In some embodiments, provided herein are charged peptide amphiphiles. Charged PAs are peptide amphiphiles containing a hydrophobic segment as described herein and a structural segment as described herein, along with a charged peptide segment. The charged segment may be acidic, basic, or zwitterionic.

In some embodiments, charged peptide amphiphiles comprise an acidic peptide segment. For example, in some embodiments, the acidic peptide comprises one or more (e.g., 1, 2, 3, 4, 5, 6, 7, or more) acidic residues (D and/or E) in sequence. In some embodiments, the acidic peptide segment comprises up to 7 residues in length and comprises at least 50% acidic residues.

In some embodiments, an acidic peptide segment comprises $(Xa)_{1-7}$, wherein each Xa is independently D or E. In some embodiments, an acidic peptide segment comprises $E_{2-4}$. For example, in some embodiments an acidic peptide segment comprises EE. In some embodiments, an acidic peptide segment comprises EEE. In other embodiments, an acidic peptide segment comprises EEEE. A charged peptide amphiphile comprising an acidic peptide segment may also be referred to herein as an "anionic PA" or an "acidic PA".

In some embodiments, charged peptide amphiphiles comprise a basic peptide segment. For example, in some embodiments, the acidic peptide comprises one or more (e.g., 1, 2, 3, 4, 5, 6, 7, or more) basic residues (R, H, and/or K) in sequence. In some embodiments, the basic peptide segment comprises up to 7 residues in length and comprises at least 50% basic residues.

In some embodiments, an acidic peptide segment comprises $(Xb)_{1-7}$, wherein each Xb is independently R, H, and/or K. A charged peptide amphiphile comprising a basic peptide segment may also be referred to herein as a "basic PA".

In some embodiments, provided herein are nanofibers and nanostructures assembled from any combination of the peptide amphiphiles described herein. In some embodiments, a nanofiber is prepared by the self-assembly of the PAs described herein. In some embodiments, a nanofiber comprises or consists of nonionic PAs. In some embodiments, in addition to nonionic PAs, charged PAs are included in the nanofibers. In some embodiments, the nonionic PAs and the charged PAs self-assemble into a nanofiber.

In some embodiments, the charged PAs (e.g., basic peptide, acidic peptides, etc.) impart mechanical characteristics to a material comprising the PA nanofibers described herein. In some embodiments, a nanofiber assembled from 0-75% (mass %) nonionic PA and 25-100% (mass %) basic charged PA becomes a gel at basic pH conditions (e.g., pH 8.5-11). In some embodiments, a nanofiber assembled from 75-100% (mass %) nonionic PA and 0-25% (mass %) basic charged PA is a liquid at basic pH conditions (e.g., pH 8.5-11). In some embodiments, a nanofiber assembled from 0-20% (mass %) nonionic PA and 80-100% (mass %) acidic charged PA becomes a gel at acidic pH conditions (e.g., pH 1-5). In some embodiments, a nanofiber assembled from 20-80% (mass %) nonionic PA and 20-80% (mass %) acidic charged PA becomes a gel at neutral pH conditions (e.g., pH 5-8.5). In some embodiments, a nanofiber assembled from 80-100% (mass %) nonionic PA and 0-20% (mass %) acidic charged PA is a liquid at acidic pH conditions (e.g., pH 1-5).

In some embodiments, nanostructures (e.g., nanofibers) comprise 100%, 95%, 90%, 85%, 80%, 75%, 70%, 65%, 60%, 55%, 50% 45%, 40%, 35%, 30%, 25%, 20%, 15%, 10%, 5%, 4%, 3%, 2%, or 1% (or any ranges there between) nonionic PAs. In some embodiments, nanofibers comprise 100% nonionic PAs. In particular embodiments, nanofibers comprise 75% nonionic PAs. For example, nanofibers may comprise 75% nonionic PAs and 25% charged PAs. For example, nanofibers may comprise 75% nonionic PAs and 25% anionic (e.g., acidic) PAs. In some embodiments, nanostructures (e.g., nanofibers) comprise 95%, 90%, 85%, 80%, 75%, 70%, 65%, 60%, 55%, 50% 45%, 40%, 35%, 30%, 25%, 20%, 15%, 10%, 5%, 4%, 3%, 2%, or 1% (or any ranges there between) acidic PAs. In some embodiments, nanostructures (e.g., nanofibers) comprise 95%, 90%, 85%, 80%, 75%, 70%, 65%, 60%, 55%, 50% 45%, 40%, 35%, 30%, 25%, 20%, 15%, 10%, 5%, 4%, 3%, 2%, or 1% (or any ranges there between) basic PAs.

In some embodiments, the ratio of nonionic PAs to acidic and/or basic PAs in a nanofiber determines the mechanical characteristics (e.g., liquid or gel) of the nanofiber material and under what conditions the material will adopt various characteristics (e.g., gelling upon exposure to physiologic conditions, liquifying upon exposure to physiologic conditions, etc.).

In some embodiments, the ratio of nonionic PAs to acidic and/or basic PAs in a nanofiber control the surface charge of the nanofiber containing the PAs. As described in detail in Example 1, varying co-assembly ratios of anionic to charged PA molecules in a nanofiber influences the surface charge of the system. Accordingly, varying the ratio of anionic to charged PA molecules allows for the production of a system having highly tunable surface charge, which may be used to influence the ability of the nanofiber to interact with cell surfaces. Moreover, modifying the surface charge of a nanofiber may also or alternatively influence bioactivity of a protein, such as a growth factor, when added to the system. In addition, modifying the spacing between PEG domains in these co-assemblies influences their ability to interact with cell surfaces. Thus, both the overall charge of PA functional groups and the spatial orientation of those groups may be modified in a system (e.g. a nanofiber) comprising anionic and charged PAs. Such modifications allow for control of the stability and bioactivity of the nanofiber, and/or control of the stability and bioactivity of a protein, such as a growth factor protein, when added to the system comprising the nanofiber.

Peptide amphiphile (PA) nanofiber solutions may comprise any suitable combination of PAs. In some embodiments, at least 0.05 mg/mL (e.g., 0.10 mg/ml, 0.15 mg/ml, 0.20 mg/ml, 0.25 mg/ml, 0.30 mg/ml, 0.35 mg/ml, 0.40 mg/ml, 0.45 mg/ml, 0.50 mg/ml, 0.60 mg/ml, 0.70 mg/ml, 0.80 mg/ml, 0.90 mg/ml, 1.0 mg/ml, or more, or ranges therebetween), of the solution is a charged PA. In some embodiments, at least 0.25 mg/mL of the solution is a charged PA. In some embodiments, a charged PA is a PA molecule having highly charged glutamic acid residues on the terminal end of the molecule (e.g., surface-displayed end). These negatively charged PAs allow for the gelation to take place between nanofibers via ionic crosslinks. In some embodiments, a charged PA is a PA molecule having highly charged lysine residues on the terminal end of the molecule (e.g., surface-displayed end). These positively charged PAs allow for the gelation to take place under basic conditions. The charged PAs provide the ability to incorporate other PAs molecules (e.g. nonionic PAs) into the nanofiber matrix while still ensuring the ability of the nanofibers solution to gel. In some embodiments, the solutions are annealed for increased viscosity and stronger gel mechanics. These charged PAs have sequences are described in, for example, U.S. Pat. No. 8,772,228 (e.g., $C_{16}$-VVVAAAEEE, e.g., $C_{16}$-VVAAEE), which is herein incorporated by reference in its entirety.

In some embodiments, the PA nanofiber described herein exhibit a small cross-sectional diameter (e.g., <25 nm, <20 nm, <15 nm, about 10 nm, etc.).

In some embodiments, the peptide amphiphile or the nanofiber comprising the PA further comprises at least one growth factor protein or a mimetic thereof. The term "mimetic" refers to a peptide that mimics the receptor binding epitope of the given growth factor. For example, a VEGF growth factor mimetic mimics the binding epitope of VEGF. In some embodiments, the growth factor protein or a mimetic thereof may be bound to the charged peptide amphiphile in the nanofiber. In some embodiments, the growth factor protein or a mimetic thereof may be bound to the charged peptide amphiphile through electrostatic interaction. For example, the negatively charged peptide segment (e.g. anionic peptide segment) of the charged peptide amphiphile may have an affinity for positively charged region(s) on the growth factor protein or mimetic thereof.

The nanofiber may comprise any suitable growth factor protein or mimetic thereof, or combination of growth factor proteins or mimetic thereof. Non-limiting examples of suitable growth factor proteins include adrenomedullin, angiopoetin, autocrine motility factor, bone morphogenic proteins (e.g. BMP-2, BMP4), ciliary neurotrophic factors (e.g., ciliary neutrophic factor, leukemia inhibitory factor, interleukin-6), colony-stimulating factors (e.g. macrophage colony-stimulating factor, granulocyte colony-stimulating factor, granulocyte macrophage colony-stimulating factor), epidermal growth factor, ephrins (e.g., ephrin A1, ephrin A2, ephrin A3, ephrin A4, ephrin A5, ephrin B1, ephrin B2, ephrin B3), erythropoietin, fibroblast growth factors, foetal bovein somatotrophin, glial cell line derived neurotrophic factor, neurturin, persephin, artemin, growth differentiation factors (e.g., GDF9), hepatocyte growth factor, hepatoma-derived growth factor, insulin, insulin-like growth factors (e.g., IGF-1, IGF-2), interleukins (e.g., IL-1, IL-2, IL-3, IL-4, IL-5, IL-6, IL-7), keratinocyte growth factor, migration-stimulating factor, macrophage-stimulating protein, myostatin, neuregulins (e.g., NRG1, NRG2, NRG3, NRG4), neurotrophins (e.g., brain-derived neurotrophic factor (BDNF), nerve growth factor, NT-3, NT-4), placental growth factor, platelet-derived growth factor, renalase, T-cell growth factor, thrombopoetin, transforming growth factors (e.g., TGF-α, TGF-β), tumor necrosis factors (e.g., TNF-α), vascular endothelial growth factor (VEGF), sonic hedgehog protein, or Wnt signaling pathway proteins. Selection of the appropriate growth factor may depend on the desired use of the nanofiber. For example, in some embodiments the growth factor may be a bone morphogenic protein (e.g., BMP-2 or BMP-4). In some embodiments, the growth factor may be a transforming growth factor (e.g., TGF-α, TGF-β). As described above, a growth factor mimetic (e.g. a mimetic of any of the above-listed growth factors) may comprise a peptide sequence that mimics the receptor binding epitope of the growth factor. For example, a VEGF growth factor mimetic comprises a peptide sequence that mimics the epitope that binds to a VEGF receptor. As another example, a BDNF growth factor mimetic comprises a peptide sequence that mimics the epitope that binds to a BDNF receptor. Accordingly, the mimetic binds to the same receptor as the growth factor protein itself, thereby affecting a similar cell signaling response.

In some embodiments, the growth factor protein or mimetic thereof may be added to a composition comprising a peptide amphiphile (e.g. a peptide amphiphile nanofiber), and may bind to the peptide amphiphile through binding to a growth factor binding sequence presented on the PA. For example, in some embodiments a peptide amphiphile further comprises a growth factor binding sequence. For example, in some embodiments the nonionic (e.g. PEGylated) PA further comprises a growth factor binding sequence. The growth factor binding sequence may be, for example, a peptide sequence. The growth factor binding sequence is presented on the peptide amphiphile, such that a growth factor can bind to the growth factor binding sequence. For example, the growth factor binding surface may be presented on the surface of a nanofiber comprising the peptide amphiphile, thus facilitating binding of an external growth factor added to the solution containing the nanofiber. In some embodiments, the growth factor binding sequence is present at the N-terminus of the peptide amphiphile. In some embodiments, the growth factor binding sequence is present at the C-terminus of the peptide amphiphile.

The PA may comprise any suitable growth factor binding sequence or combination of sequences to bind to the desired growth factor protein(s). The growth factor binding sequence may be any suitable sequence that binds to, for example, a growth factor listed above. The growth factor binding sequence may be a charged peptide sequence or an uncharged peptide sequence.

In some embodiments, the growth factor is a member of the TGF-β family of growth factors. The TGF-β family of growth factors includes, for example, TGFβ-1, bone morphogenic protein subfamily (e.g. BMP-2, BMP-4), the growth differentiation factors subfamily, the activin and inhibin subfamilies, the left-right determination factors, and other various members.

Exemplary growth factor binding sequences are shown in Table 1 below. Note that these sequences are only intended to exemplify possible binding sequences, and other suitable sequences may be used.

TABLE 1

Binding sequences for BMP-2 and TGF-β1

| TBF-B1 binding sequence | SEQ ID NO: | BMP-2 Binding Sequence | SEQ ID NO: |
|---|---|---|---|
| HSNGLPL | SEQ ID NO: 1 | YPVHPST | SEQ ID NO: 11 |
| LPLGNSH | SEQ ID NO: 2 | LHYPFMT | SEQ ID NO: 12 |
| LRNYSHS | SEQ ID NO: 3 | KQALTQT | SEQ ID NO: 13 |
| VYRHLPT | SEQ ID NO: 4 | WPALFTH | SEQ ID NO: 14 |
| RVSTWDT | SEQ ID NO: 5 | PGPTVQG | SEQ ID NO: 15 |
| PAPRWIH | SEQ ID NO: 6 | LHYPFMT | SEQ ID NO: 16 |
| RTTSPTA | SEQ ID NO: 7 | QQTQAQH | SEQ ID NO: 17 |
| GKYPPTS | SEQ ID NO: 8 | PIQPDER | SEQ ID NO: 18 |
| AWKSVTA | SEQ ID NO: 9 | PFDPPVR | SEQ ID NO: 19 |
| LPSPIQK | SEQ ID NO: 10 | DVSPAYH | SEQ ID NO: 20 |

For example, in some embodiments the growth factor is TGFβ-1 and the growth factor binding sequence is HSNGLPL (SEQ ID NO: 1). In some embodiments, the growth factor is BMP-2 and the growth factor binding sequence is a peptide sequence that binds to BMP-2. In some embodiments, the growth factor is BMP-4 and the growth factor binding sequence is a peptide sequence that binds to BMP-4.

In some embodiments, the growth factor is a mimetic peptide. For example, in some embodiments the growth factor is the VEGF mimetic peptide IGKYKLQYLEQWTLK (SEQ II) NO: 21) or D(IG-KYKLQYLEQWTLK) (SEQ ID NO: 22).

In some embodiments, the bioactivity and or circulating time of the growth factor may be enhanced due to the presence of the nonionic (e.g. PEGylated) PA in the nanofiber. For example, the nonionic PA may allow for control of the surface charge of the nanofiber, thereby stabilizing the attached growth factor. This stabilization may lead to enhanced efficacy by increasing circulating time in vivo or stabilizing the bioactivity of the growth factor protein.

In some embodiments, selection of the appropriate PA may dictate the purification conditions that may be employed to isolate the PA. This may be particularly important for embodiments where the PA contains a growth factor binding sequence, which can undergo undesirable changes during purification in basic and/or acidic conditions. For example, in some instances it may be desirable to avoid basic purification conditions, which may otherwise be detrimental to a growth factor binding sequence present on the PA. For example, the use of an anionic (e.g. PEGylated) PA may render the PA incompatible with basic purification conditions which would otherwise be detrimental to a growth factor binding sequence present on the PA. Accordingly, in some aspects provided herein is a PEGylated PA comprising a growth factor binding sequence that may be isolated in acidic conditions (e.g. by HPLC in acidic conditions), thereby preventing undesirable changes to the growth factor binding sequence and retaining the ability of the growth factor binding sequence to bind and promote the enhanced stability and/or bioactivity of the growth factor protein.

In some embodiments, provided herein are compositions comprising a nonionic peptide amphiphile or a nanofiber containing the same. In some embodiments, the compositions further comprise a charged peptide amphiphile. The composition may further comprise one or more pharmaceutically acceptable carriers. For example, the composition may further comprise one or more pharmaceutically acceptable carriers for delivery to a cell or a subject.

The PAs, nanofibers, and compositions described herein find use in a variety of methods. In some embodiments, provided herein is a method comprising contacting a cell with a composition as described herein. The cell may be isolated from a subject prior to contact with the composition. The cell may be administered to the same or a different subject following a suitable time after contact with the composition. For example, the cell may be contacted with a composition to promote differentiation into a desired cell or tissue type, and that cell or tissue may be administered to the same or a different subject. For example, the method may comprise contacting a cell with a composition containing a nanofiber as described herein (e.g. a nanofiber containing a nonionic PA and a charged PA). In some embodiments, the nanofiber further contains a growth factor (e.g. a growth factor protein, which may be bound to the charged PA or which may bind to a growth factor binding protein attached to the PEGylated PA). For example, the method may comprise contacting a cell with a composition containing a nanofiber comprising a nonionic PA containing a growth factor binding sequence. An external growth factor may be added, either to the nanofiber prior to contact with the cell or to the system comprising the cell and the nanofiber, and the growth factor may bind to the growth factor binding sequence on the nanofiber. The use of such a nanofiber, such as a PEGylated nanofiber, may prolong the bioactivity and/or increase the stability of the growth factor.

Contacting the cell with the nanofiber or composition comprising the same may promote differentiation of the cell. For example, the cell may be a stem cell. Suitable stem cells include, for example, mesenchymal stem cells or neural stem cells. A suitable stem cell may be selected and contacted with a composition or nanofiber described herein to promote differentiation of the cell into the desired type, such as for use in tissue engineering or regenerative medicine. For example, BMP-2 is, amongst others, involved in the formation of bone and the development of the brain and the dorsal spinal cord, whereas TGF-β1 is implicated in the formation of cartilage and the differentiation of smooth muscle cells. The corresponding nanofibers may thus be contacted with a cell population to control the differentiation of, for example, mesenchymal stem cells. Mesenchymal stem cells have been shown to differentiate in vitro and in vivo into a variety of lineages like bone, cartilage, fat, muscle cells and myocardium and may be useful for a variety of therapeutic purposes.

In some embodiments, compositions containing a nanofiber as described herein may be used in the fields of regenerative and transplant medicine. In some embodiments, the compositions may be used for regenerative therapies. For example, the compositions may be used in methods repair or regeneration of an area in a subject in need thereof. In some embodiments, the compositions are used for regeneration of a bone or tissue in a subject in need thereof. The compositions may be used for the regeneration of any tissue, including bodily tissue (e.g., soft tissue), bone regeneration, neural regeneration, skeletal tissue construction, repair of muscle injuries, the repair of cardio-vascular injuries, the expansion and self-renewal of embryonic- and adult stem cells, etc. For example, compositions described herein may be used to prevent or treat a wide range of diseases and injuries, including: soft tissue wound repair, regeneration of the brain or spinal cord (e.g. following stroke, traumatic injury, etc.) post-surgical healing, osteoarthritis, cartilage replacement, broken bones of any kind (e.g. spinal disc fusion treatments, long bone breaks, cranial defects, etc.), critical or non-union bone defects, etc. For example, the peptide amphiphiles may be used with suitable growth factors or may contain suitable binding sequences for a desired growth factor to be applied for regenerative therapy for a wide variety of tissues or the support of transplanted tissues in a patient. For example, since BMP-2 and TGF-β1 play an important role in osteoblastic and chondrogenic differentiation of mesenchymal stem cells, respectively, the compositions described herein may be used for regeneration of bone and cartilage. BMP-2 also plays an important role in the formation of the brain and the dorsal spinal cord. Therefore, the compositions can also be used in combination with neural stem cells for the regeneration of damaged spinal cord and/or to repair damaged brain areas in the case of stroke.

In some embodiments, the compositions described herein are formulated for delivery to a subject. In some embodiments, the compositions are administered parenterally. The term "parenteral" refers to any suitable non-oral route of administration, including subcutaneous, intramuscular, intravenous, intrathecal, intracisternal, intraarterial, intraspinal, intraepidural, intradermal, and the like. The PA compositions herein can be administered as the sole active agent or in combination with other pharmaceutical agents. For example, the compositions can be administered in combination with other agents for regenerative therapy in a subject.

EXAMPLES

Example 1

Described herein is an uncharged PA molecule (e.g. nonionic PA) and a demonstration of how absolute ionic charge controls self-assembly and bioactivity of PA filaments.

Experimental Section

PA synthesis and purification: All PA molecules were synthesized using standard Fmoc synthesis on a Rink amide resin as previously reported.[35] For standard couplings, four equivalents of the amino acid was added in dimethyl formamide with six equivalents of diisopropylethylamine (DIEA) and 3.95 equivalents 2-(1H-B enzotriazole-1-yl)-1,1,3,3-tetramethyluronium hexafluorophosphate (HBTU). For the PEG-10 amino acid (ChemPEP, Wellington, Florida, USA), 1.5 equivalents were added in dimethyl formamide with an equal concentration of (Benzotriazol-1-yloxy)tripyrrolidinophosphonium hexafluorophosphate (PyBOP) and 2 equivalents of DIEA overnight. Following coupling of the palmitic acid tail, peptides were cleaved from the resin in a 95:2.5:2.5 trifluoroacetic acid (TFA)/triisopropylsilane/water mixture for 3 hours and precipitated in cold diethyl ether. The crude peptide was dissolved in 0.1% TFA (PA1, PA3, and PA5) or 0.1% ammonium hydroxide (PA2, PA4) and purified by high-performance liquid chromatography (HPLC). PA1 was purified against a 5% to 95% gradient of water to a mixture of 75% acetonitrile and 25% tetrahydrofuran (THF), while all other PA molecules were purified over a 5 to 95% gradient of water to acetonitrile. All PA molecules were lyophilized following purification. For PA1, the dehydrated peptide was rehydrated and then lyophilized twice to remove any excess THF. The purity of the PA molecules was confirmed to be above 95% by liquid chromatography—electrospray ionization mass spectrometry using an Agilent 6520 quadrupole time-of-flight (Q-TOF) ESI-MS instrument over a 5% to 95% water to acetonitrile gradient.

Solubilization and Heat Treatment: PA powders were resuspended to 10 mM in water for experiments at pH 7, in 10 mM hydrochloric acid for pH 2 and 10 mM sodium hydroxide for pH 12. After resuspension, 1 M sodium hydroxide or 1 M hydrogen chloride were added to achieve the desired pH. To co-assemble PA molecules, PA solutions were mixed volumetrically, bath sonicated for 1 hour and then left on the bench to age for at least 2 hours. A solution of 150 mM NaCl was added to all samples to achieve a final NaCl concentration of 30 mM. All samples were heat treated at 80° C. for 30 minutes followed by gradual cooling by 1° C. per minute to 25° C.

Nile Red Assay: Following heat treatment, PA solutions were serially diluted in water (0 mM NaCl), or a buffer of 15 mM NaCl, or 150 mM NaCl. A solution of 100 μM Nile red was added to the PA solutions to one thousandth the total volume and incubated for 1 hour. The fluorescence spectrum was read from 600 nm to 700 nm using a BioTek Cytation 3 microplate reader using 560 nm excitation and the fluorescence shift was determined by subtracting the maximum excitation wavelength for each sample from that of the dye solution diluted in each buffer alone.

X-ray scattering: SAXS and WAXS measurements were obtained simultaneously at the Dupont-Northwestern-Dow Collaborative Access Team Synchrotro n Research Center at the Advanced Photon Source at Argonne National Lab using beamline 5ID-D. Heat treated PA samples were flowed through a 1.5 mm glass capillary at 1 mm/sec during x-ray exposure for consistent background subtraction with buffer only samples. Five exposures of 10 seconds were obtained using 17 keV monochromatic x-rays using a CCD detector which was 245 cm behind the sample. The collected two-dimensional scattering images were averaged by azimuthal integration using FIT2D software. Intensities were plotted background subtracted and plotted against the wave vector $q=(4\pi)\sin(\theta/2)$ where $d=2 \pi/q$.

Circular Dichroism: For ionic strength experiments, heat treated PA solutions were diluted 200 times in water, 15 mM NaCl, or 150 mM NaCl prior to measurement. For all other experiments, PA solutions were diluted in a buffer of either 10 mM HCl and 10 mM NaCl, 10 mM NaCl, or 10 mM NaOH and 10 mM NaCl for measurements at pH 2, pH 7, and pH 12 respectively. CD spectra were acquired on a J-815 CD spectrophotometer (Jasco Analytic Instruments, Easton, Maryland) in a 2 mm quartz cuvette. The average of 3 measurements over 250 nm to 190 nm was recorded.

Zeta potential: Heat-treated PA solutions were diluted 20 times in 30 mM NaCl with 10 mM HCl, 30 mM NaCl, or 30 mM NaCl with 10 mM NaOH for pH 2, pH 7, and pH 12 respectively. For each PA, three separate samples were prepared at each pH. Samples were loaded in a disposable folded capillary cell and zeta-potential was measured at 25°

C. using a Zetasizer Nano ZS (Malvern Instruments, Malvern, UK). The average of the three measurements for each sample was plotted.

Transmission Electron Microscopy: TEM was performed on PA solutions preserved in vitreous ice on a JEOL 1230 TEM with a Gatan 831 CCD camera using an accelerating voltage of 100 kV. Samples were diluted with milli-Q water to 1 mM immediately prior to blotting. Copper mesh TEM grids with lacey carbon support (Electron Microscopy Sciences) were treated with glow discharge and then 7 µl of sample was pipetted onto the grid. Samples were blotted twice and plunged into liquid ethane using a Vitrobot Mark IV instrument (FEI) with 95-100% humidity in the chamber at 20° C. Samples were then transferred to a Gatan 626 cryo-holder under liquid nitrogen for imaging.

Fourier transform infrared spectroscopy (FT-IR): Following heat treatment, PA solutions were lyophilized and then reconstituted in $D_2O$ after which samples were heat treated a second time. For measurement, PA solutions were placed between two CaF2 windows spaced 50 µm apart and a Bruker Tensor 27 spectrometer was used to measure transmittance. Solvent background was subtracted from the obtained spectrum and plotted against the wavenumber.

Cytotoxicity: Normal Human Lung Fibroblasts were obtained from Lonza and maintained in growth medium consisting of DMEM with 10% fetal bovine serum (FBS) and 1% penicillin/streptomycin. Cells (passage 5) were tryspinized and resuspended in media containing 2% FBS and 150 µl of the cell suspension was added to each well of a 96 well microplate for a total of 2,500 cells per well. After 2 hours attachment, 50 µl PA solutions diluted in PBS to 4 µM, 20 µM, 100 µM, or 400 µM were added to each well. After 36 hours culture, the media was removed and replaced with a solution of 2 µM calcein and 4 µM ethidium homodimer in PBS. After 30 minutes, cells were imaged using a Cytation 3 microplate reader. Live and Dead cells were counted using the MATLAB image Processing Toolbox to determine viability.

Alkaline Phosphatase Activity: Human mesenchymal stem cells were obtained from Lonza and maintained in Mesenchymal Stem Cell Growth Media (Lonza). Cells were used for experiments prior to passage 6. Cells were trypsinized and resuspended in growth media containing high glucose DMEM supplemented with 10% FBS and 1% penicillin/streptomycin and 50 mg/L sodium ascorbate. 500 µl of the cell suspension was placed in each well of a 24 well plate and incubated for 24 hours. Media was removed and replaced with 540 µl of growth media or osteogenic media containing low glucose DMEM supplemented with 10% FBS, 50 mg/L sodium ascorbate 10 mM 3-glycerophosphate, and 100 nM dexamethasone. 60 µl of a 10 times concentrated PA solution in PBS was then added to each well. Every 3-4 days, media was replaced by removing 300 µl media and adding 270 µl growth media or osteogenic media and 30 µl of the 10 times concentrated PA solution in PBS. Alkaline phosphatase (ALP) activity was determined using the SensoLyte pNPP ALP Assay Kit (Anaspec, Fremont, CA) according to the manufacturer's instructions. Briefly, cells were washed once with the assay buffer and the 200 µl of the assay buffer supplemented with Triton-X was added to each well. The plate was incubated for 1 hour at 4° C. under mild agitation, cells were scraped with a pipette tip and collected, and the suspension was centrifuged for 10 minutes at 5,000 g. The supernatant was mixed with the assay's detection buffer in a microplate and the optical absorbance was read after a four-hour incubation using a Cytation 3 microplate reader. The supernatant was also used to determine DNA concentration using a Quant-iT PicoGreen dsDNA kit (Molecular Probes, Eugene, OR). ALP concentration was normalized to DNA concentration for each sample.

Results

Self-Assembly of Nonionic PA Filaments

Figure 2A:
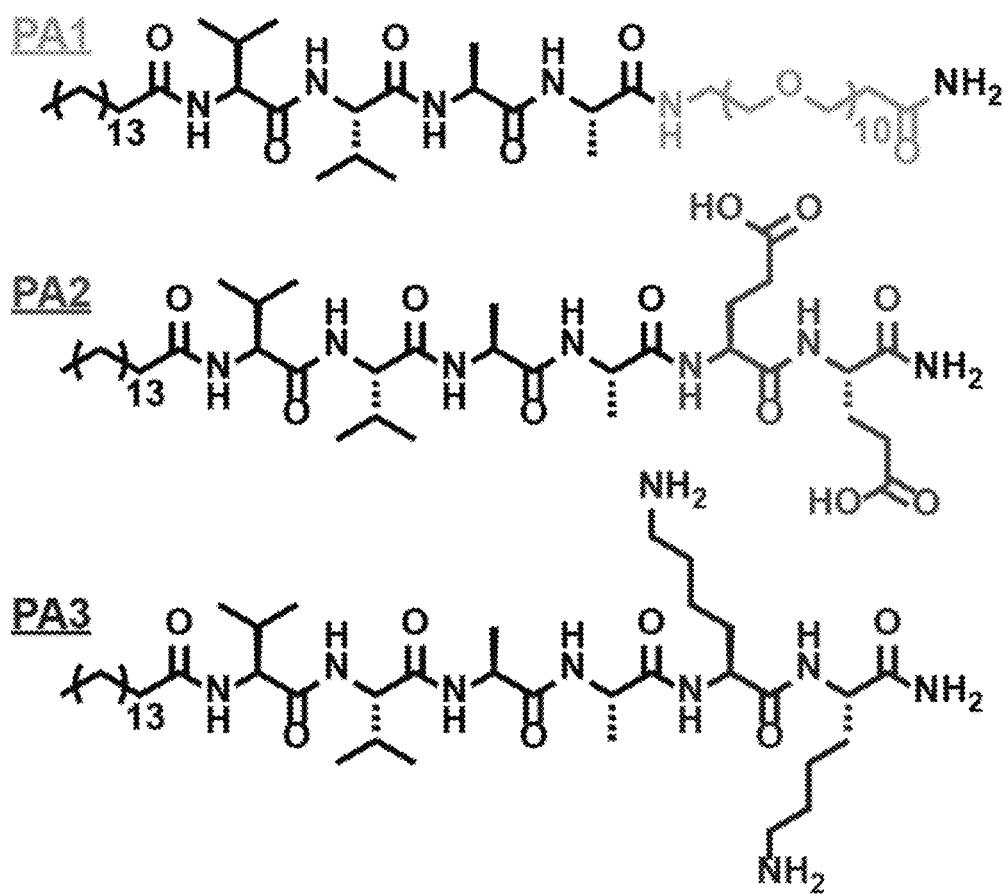
(FIG. 2A) Structures of the uncharged PA1, the anionic PA2, and the cationic PA3.

To produce PA filaments without ionic charge, a short PEG chain was substituted for the ionizable amino acids typically included in PA molecules to maintain solubility of the PA in an aqueous environment. To form an uncharged PA filament, the sequence N-palmitoyl-VVAA was chosen as the aliphatic tail and hydrogen bonding peptide. As the hydrophilic domain, a 10-mer PEG amino acid was selected, which was hypothesized to be long enough to solubilize the PA while limiting steric repulsion among assembled molecules (PA1, FIG. 2A). The PA was synthesized by coupling the PEG amino acid to a rink-amide resin and completing the peptide using standard Fmoc solid phase peptide synthesis, leaving an uncharged amide group after cleavage from the resin. Following synthesis, the purified molecule was readily resuspended in water, giving a cloudy solution without a noticeable change in viscosity. As ionic control molecules, the PEG domain was replaced with either two glutamic acid residues (PA2, FIG. 2A), or two lysine residues (PA3, FIG. 2A) as anionic and cationic counterparts, respectively.

Figure 3:
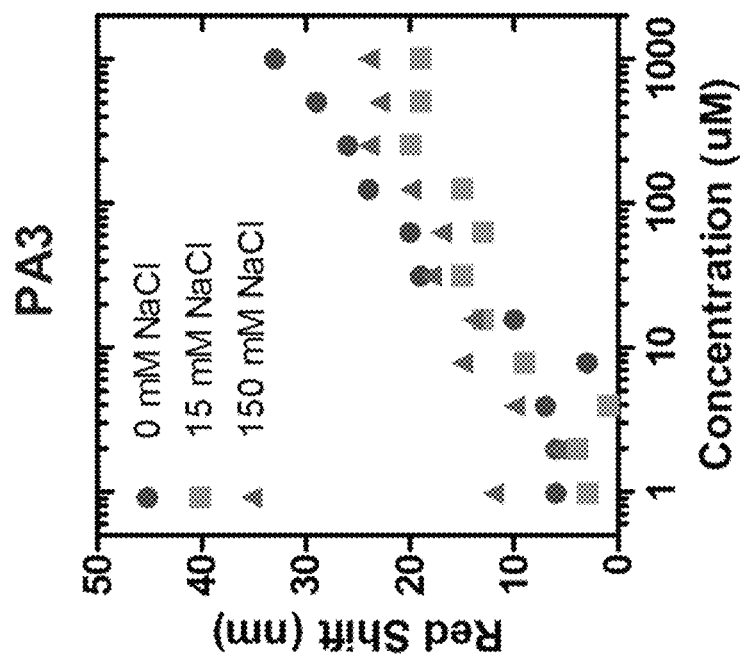
FIG. 3. Redshift of peak Nile red fluorescence as a function of PA3 concentration in buffers of 0 mM, 15 mM, and 150 mM NaCl.
Figure 4:
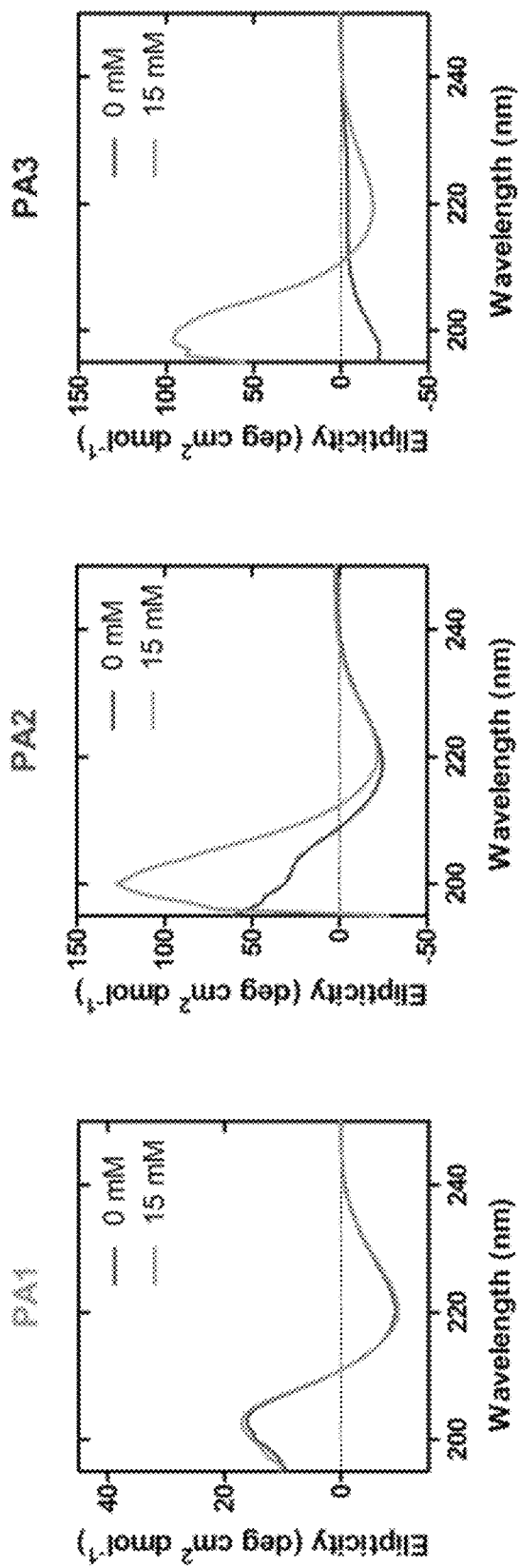
FIG. 4. Circular dichroism of PA solutions plotted as a function of wavelength in 0 mM NaCl buffer and in 15 mM NaCl buffer.
Figure 5:
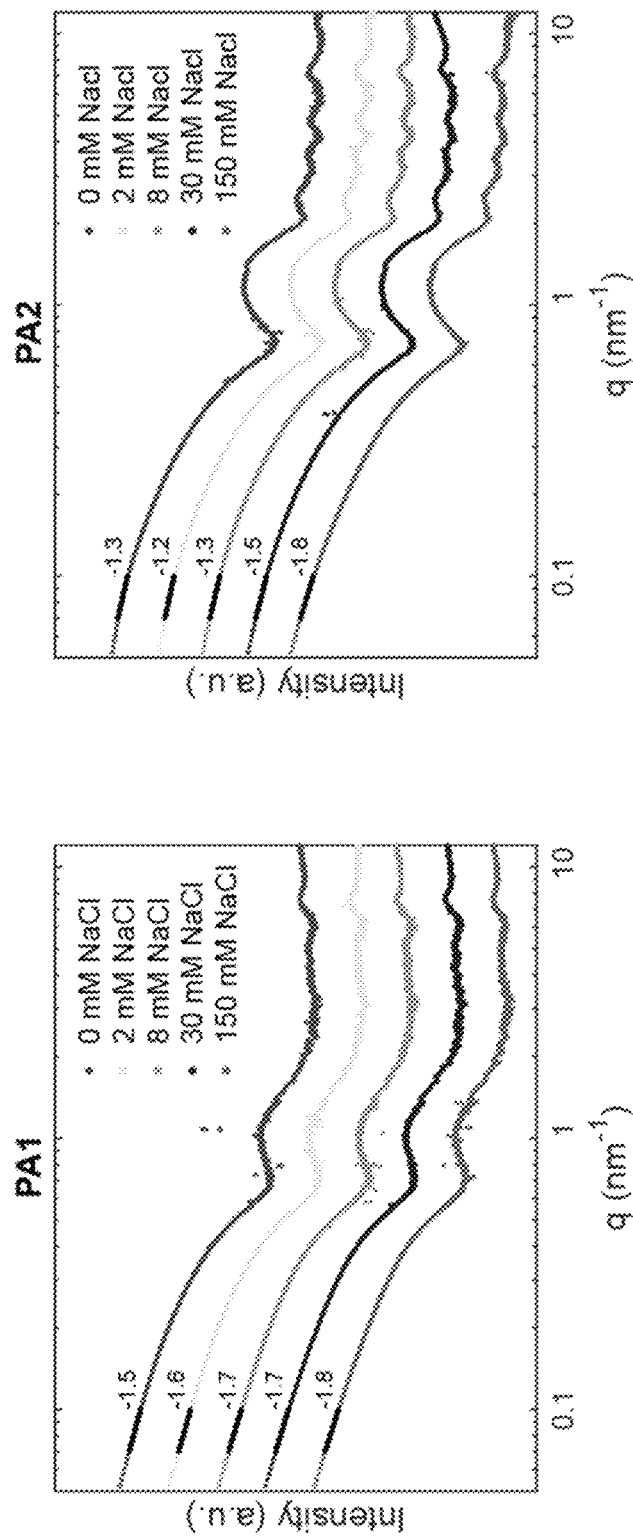
FIG. 5. Scattering intensity patterns for PA1 (left panel) and PA2 (right panel) solutions in buffers of 0 mM, 2 mM, 8 mM, 30 mM, and 150 mM NaCl.
Figures 6A, 6B:
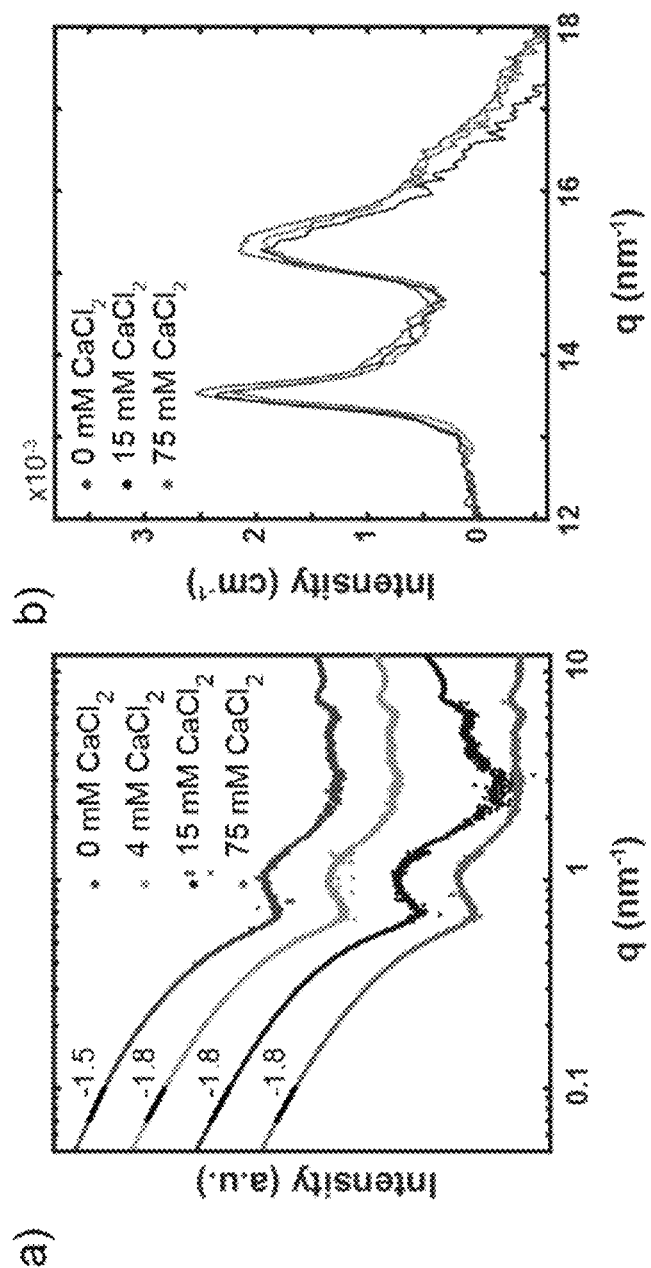
(FIG. 6A) SAXS intensity and (FIG. 6B) WAXS intensity as a function of the wave vector for PA1 in buffers of variable $CaCl_2$ concentration.

It was next assessed how the elimination of charge via PEGylation affected assembly of the PA molecules. In non-PA self-assembling peptides, appended PEG chains can strengthen secondary interactions among molecules[37] and can increase critical micelle concentration due to increased steric repulsion.[38] In charged PA molecules, assembly occurs when hydrophobic collapse of the alkyl domain balance electrostatic repulsion between neighboring molecules. Because PA1 lacks ionic residues, it was hypothesized that the molecule could self-assemble at lower concentrations than its charged counterpart. Aggregation of the molecules was monitored using the Nile red assay where a redshift in the dye's fluorescence emission is correlated with the emergence of hydrophobic pockets as amphiphiles assemble.[39] Aggregation of PA1 as indicated by the redshift in Nile red fluorescence occurred independently of ionic strength, while PA2, aggregation depended on ionic strength of the buffer, with smaller shifts recorded in 0 mM and 15 mM NaCl than in 150 mM NaCl (FIG. 2B). In 0 mM and 15 mM NaCl, aggregation curves for PA2 shifted to a higher concentration than PA1, indicating that charge screening is not required to induce assembly of the uncharged PA (FIG. 2B). The apparent redshift in the fluorescence peak of Nile red co-assembled with PA3 was less dependent on ionic strength than PA2, though at higher concentrations the redshift was about half that of PA1 or PA2, suggesting the dye may not have completely intercalated in the assemblies (FIG. 3). PA1 produced nearly identical circular dichroism (CD) spectra with and without salt, while the spectra for PA2 and PA3 were salt dependent showing clear β-sheet with 15 mM NaCl but not without added salt (FIG. 4). Small angle x-ray scattering (SAXS) patterns of 8 mM solutions for both PA1 and PA2 showed form factors consistent with filament formation with and without NaCl in the buffer, suggesting the sodium hydroxide added to adjust PA2 solutions to pH 7 provided sufficient screening for the supramolecular structures to form (FIG. 5). Interestingly, despite significant differences in the geometry of their hydrophilic regions—a linear, nonionic PEG chain for PA1 and branched ionizable glutamic acid residues for PA2—the filaments formed by both PA molecules had similar internal order with wide-angle x-ray scattering (WAXS) showing Bragg peaks corresponding to d-spacings of 0.47 nm and 0.41 nm (FIG. 2C). The intensity of these peaks decreased with increasing ionic strength for PA1, but increased with increasing ionic strength for PA2, presumably due to stabilization of the structure through decreasing charge repulsion among the molecules. While divalent cations can affect self-assembly of anionic PAs,[40] replacing NaCl with $CaCl_2$ had little effect on PA1 self-assembly (FIG. 6), highlighting the ability of the molecule to form similar filaments despite significant changes in buffer conditions.

pH Dependence of PA Filament Assembly

Figure 7A:
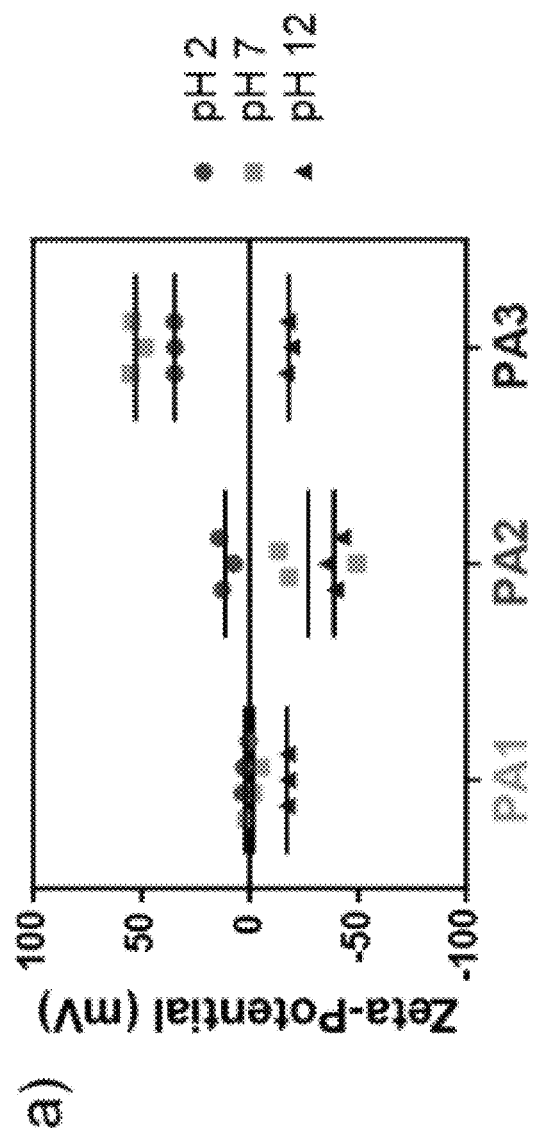
(FIG. 7A) Zeta-potential measurements for PA1, PA2, and PA3 solutions at $pH_2$, pH 7, and pH 12.
Figure 7B:
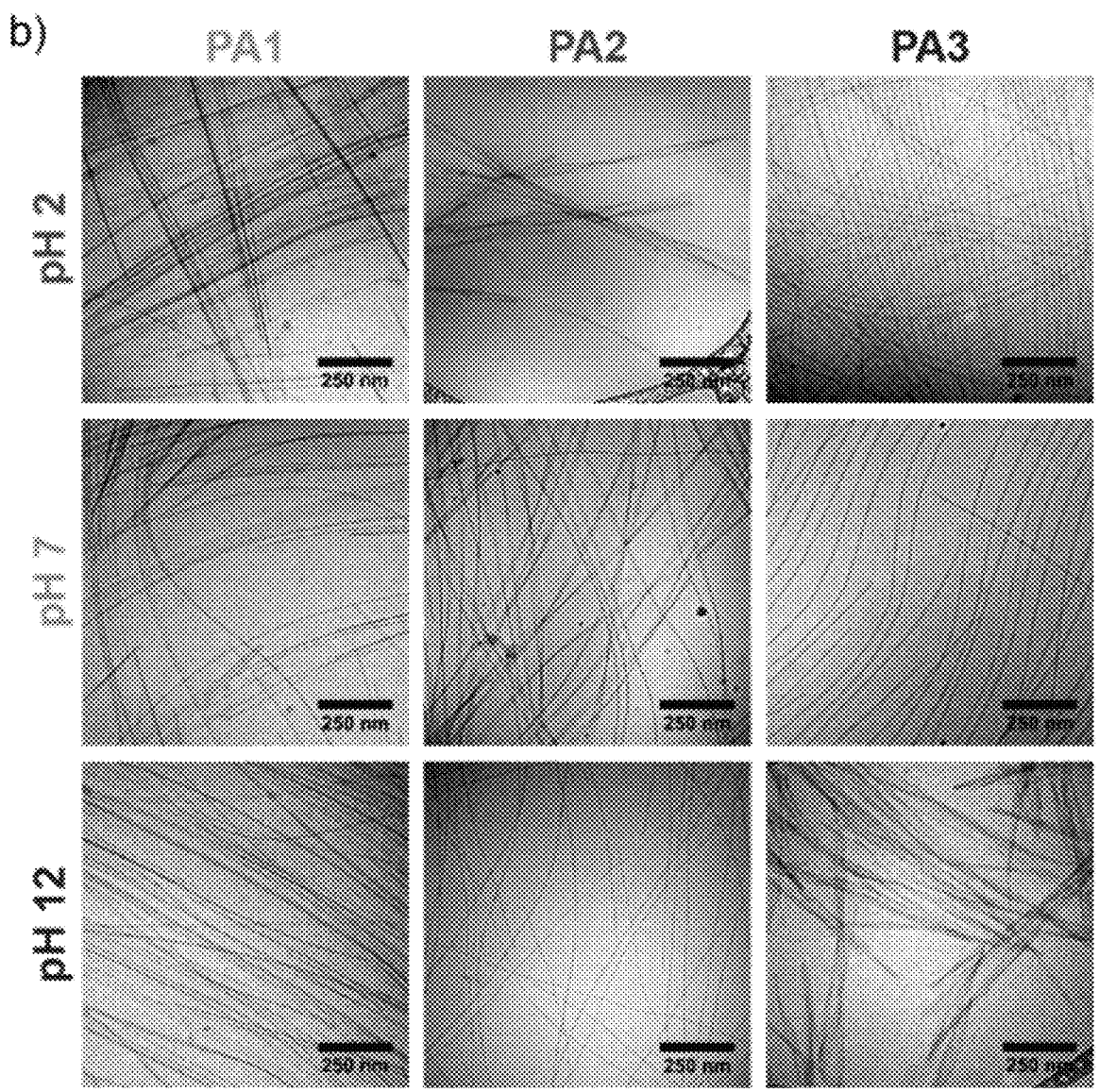
(FIG. 7B) Cryo-TEM images of PA1, PA2, and PA3 each prepared at $pH_2$, pH 7, and pH 12 and preserved in vitreous ice.

Zeta-potential measurements confirmed that the surface charge of PA1 was near 0 mV at pH 2, pH 7, and pH 12, while surface charge was pH-dependent for PA2 and PA3, which were respectively negatively- and positively charged at neutral pH (FIG. 7A). Cryo-TEM of samples preserved in vitreous ice showed that PA1 uniformly formed narrow ribbon structures at all pHs tested while observed morphologies of PA2 and PA3 assemblies were pH-dependent. At low pH, PA2 formed wide, short ribbons that bundled with each other, but at and above neutral pH PA2 formed longer, narrow fibers. Similarly, PA3 formed wide, short, bundled structures at high pH, but formed narrow, longer filaments when charged at neutral pH and below (FIG. 7B).

These observations are supported by SAXS scattering data which showed that PA1 produced a scattering pattern at pH 2, pH 7, and pH 12 that was uniformly consistent with the ribbon-like structures observed on TEM. In contrast, the scattering pattern for PA2 changed significantly with increasing pH; the low-q slope transitioned from −3.5 at low pH consistent with aggregate formation to −1.2 and −0.9 at neutral and basic pH, consistent with more cylindrical filaments. Similarly, the low-q slope of PA3 changed from −2.2 at pH 12 indicating planar structures to −1.1 at pH 7 and −1 pH 12, indicating the formation of cylindrical filaments as charge increased (FIG. 7C). CD also demonstrated the degree of dependence of self-assembly on pH for each of the three PAs. PA1 formed (3-sheet in acidic, neutral, and basic conditions, with similar patterns observed at all three pH values. In PA2, (3-sheet character decreased with increased pH as acidic groups were deprotonated and repelled one another (FIG. 7D). CD spectra for PA3 were not significantly pH dependent, suggesting repulsion among protonated lysine residues had less of an impact on (3-sheet formation among the molecules than deprotonation of glutamic acid residues. This may be due to the smaller distance between the charged group and the peptide backbone for glutamic acid than for lysine or increased delocalization of the ionic charge in glutamic acid relative to lysine.

To determine if the observed pH independent behavior was a result of PEGylation alone and not the nonionic design of PA1, two control molecules extending PA2 and PA3 with the 10-mer PEG amino acid were synthesized to make N-palmitoyl-VVAAEE-$PEG_{10}$ (PA4, FIGS. 8A) and N-palmitoyl-VVAAKK-PEGio (PA5, FIG. 8A). Zeta-potential measurements showed that these molecules had a smaller range of surface charge over the pH range tested compared to their non-PEGylated counterparts, yet were near 0 mV only at pH 2 for PA4 and pH 12 for PA5 (FIG. 8B). SAXS showed that self-assembly of these molecules was pH dependent like the charged, non-PEGylated PA molecules tested, with low-q slope dependent on surface charge (FIG. 9A). CD further confirmed that (3-sheet formation by PA4 and PA5 was also pH dependent, with CD spectra showing (3-sheet formed only when charge was minimal (pH 2 for PA4 and pH 12 for PA5; Figure FIG. 9B). Thus, pH-independent self-assembly by these PA molecules is achieved only by the removal of readily ionized groups, not merely extending the hydrophilic region of the molecule with PEG moieties.

Co-assembly of Nonionic and Ionic PAs

Figure 10A:
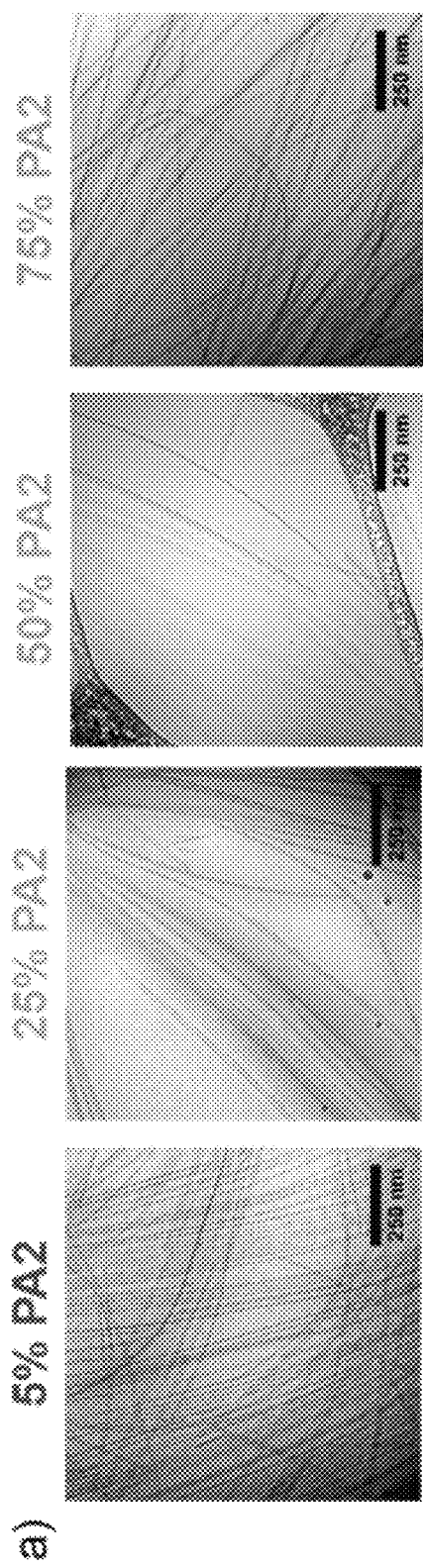
(FIG. 10A) Cryo-TEM micrographs of co-assemblies of nonionic PA1 and anionic PA2 preserved in vitreous ice with the molar fraction of PA2 in the co-assemblies indicated.
Figure 10B:
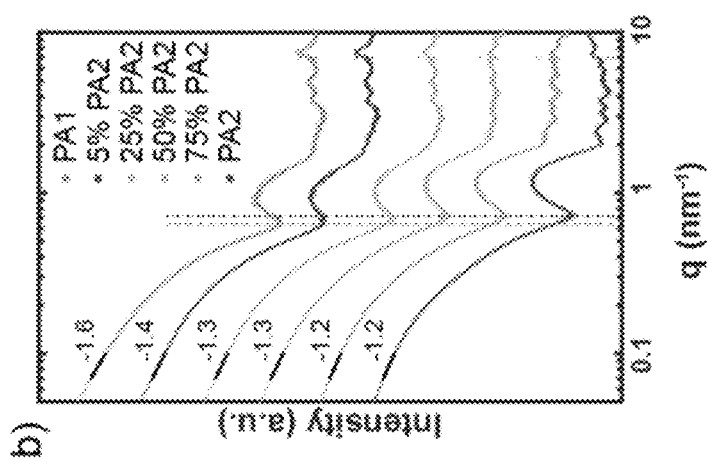
(FIG. 10B) Scattering intensities of the co-assembled PA systems as a function of the wave vector with vertical lines showing the first minimum of the PA1 and PA2 patterns.
Figures 10C, 10D, 10E:
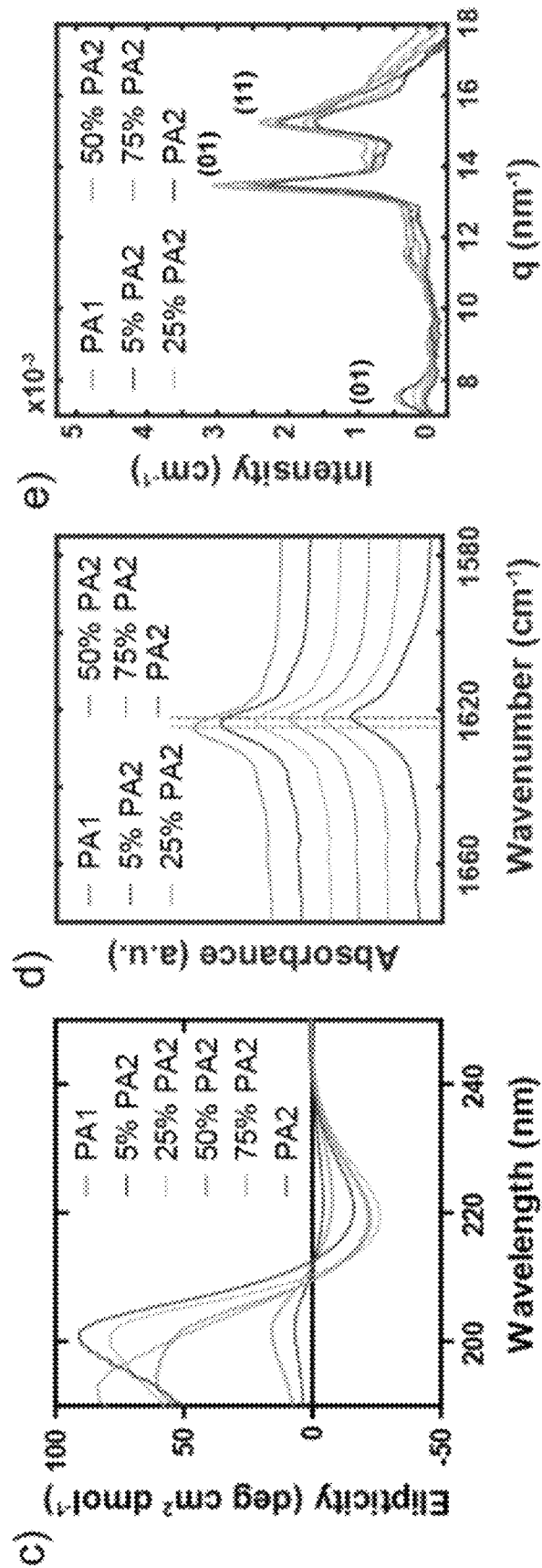
(FIG. 10C) CD as a function of wavelength for the co-assembled PA systems.
(FIG. 10D) FTIR absorbance as a function of wavenumber for the co-assembled PA systems with vertical line showing the peak absorbance in the amide I' band for PA1 and PA2.
(FIG. 10E) WAXS intensity as a function of the wave vector for the co-assembled PA systems.

To produce PA filaments with controlled amounts of surface charge, co-assembled solutions of nonionic PA1 with anionic PA2 were prepared by mixing solutions of the individual PA molecules in a 30 mM NaCl buffer and sonicating prior to heat treatment. In this system, both the nonionic and ionic surfactant components are peptides, allowing for the study of how changing the ratio of nonionic and ionic components affects interactions among the hydrogen-bonding peptide domains. Cryo-TEM of the co-assemblies showed the addition of 5% PA2 to PA1 assemblies formed similar narrow ribbons to those observed in PA1 alone. With the addition of 25% PA2 or more, the resulting filaments appeared more similar to the broader, twisting ribbons formed by assemblies comprising entirely PA2, suggesting only a fraction of the molecules must be charged to produce the charged system morphology (FIG. 10A, see FIG. 7B). Consistent with this trend, SAXS showed significant changes in low-q slope with the addition of a small fraction of PA2 to the uncharged PA1 filaments, with 75% of the change in slope occurring with the addition of only 25% PA2, indicating a transition from ribbon-like to cylinder-like assemblies. Similarly, the first minimum in the pattern shifted to the right as uncharged PA1 molecules were replaced with the charged PA2 with the most significant change occurring with 25% or less PA2 added to the assemblies (FIG. 10B). For co-assemblies of PA1 and the cationic PA3, low-q slope changed more gradually with the addition of charged groups (FIG. 11A), which may further suggest electrostatic repulsion among lysine residues affects assembly morphology less than repulsion among glutamic acid residues. CD spectra showed weaker overall (3-sheet signal for PA1 alone and co-assemblies containing 5% PA2, but with the addition of only 25% PA2 the (3-sheet signal had similar intensity to the fully charged PA2 filaments (FIG. 10C).

As an additional technique to study intermolecular interactions within the co-assemblies, Fourier-transform infrared spectroscopy (FTIR) was used to monitor the Amide I' peak, which is sensitive to hydrogen bonding among the peptides. A lower wavenumber peak position was observed for PA2 relative to the nonionic PA1, and when the two molecules were co-assembled, the shift in peak position occurred with the addition of only 25% PA2 (FIG. 10D). Previous reports of alanine-rich peptides indicate that this shift is correlated with hydration of the peptides, suggesting increasing charge leads to increased solvation of the hydrogen-bonding region.[42] Together, these data suggest the existence of nonionic-like assemblies to ionic-like assemblies, with co-assemblies of charged uncharged PA molecules forming ionic-like assemblies even when a minority of the PA molecules are charged. Thus, charge repulsion among a minority of PA molecules within the assembly is sufficient to determine intermolecular order of both the ionic and nonionic molecules within the filaments.

Using WAXS, it was next investigated how changing the total charge affects the spatial arrangement of molecules within the assembled filaments. Three peaks were observed, the first at a d-spacing of 0.84 nm is a result of the (01) spacing between the (3-strands, the second peak with a d-spacing of 0.47 nm results from the (10) reflection, and the third peak corresponding to a d-spacing of 0.41 nm results from a (11) reflection. The intensity of the (01) and (11) peaks are stronger in the fully nonionic system than in the fully anionic assemblies. This may be due to the directionality of the repulsive interactions among the molecules. Because the ionic charges are located on sidechains extended perpendicular to the (β-strands, repulsion among neighboring strands affects inter-strand spacing, while steric repulsion among PEG chains is more likely to affect interactions with the nearest neighbor only. When the two components are co-assembled, the strongest (10) peak occurs at 50% PA1 and 50% PA2, where alternating non-ionic and ionic PA molecules may separate PEG chains and separate anionic side chains within the β-strand, limiting repulsion among the molecules (FIG. 10E). For co-assemblies of PA1 and the cationic PA3, the intensity of all three peaks decreased with increasing charged PA content (FIG. 11B), possibly due to increased flexibility of the lysine side chain. These results suggest that the effects of steric or electrostatic repulsive interactions among PA molecules depends on their ordering within the PA.

Effect of Surface Charge on PA Bioactivity

Figure 12A:
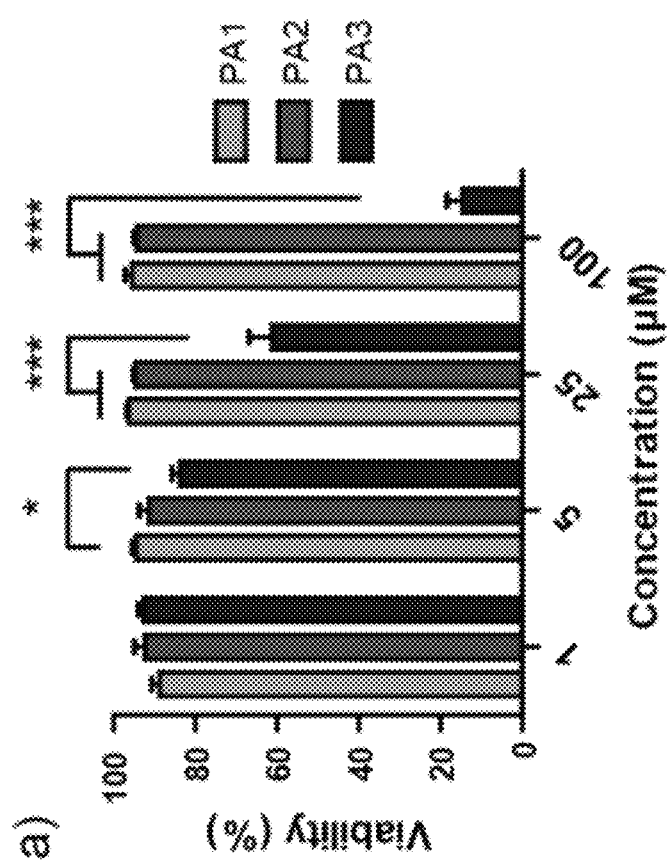
(FIG. 12A) Percent viable cells as a function of PA concentration for nHLF cultures treated with PA1, PA2, or PA3; significance calculated relative to other PA solutions at the same concentration.
Figure 13:
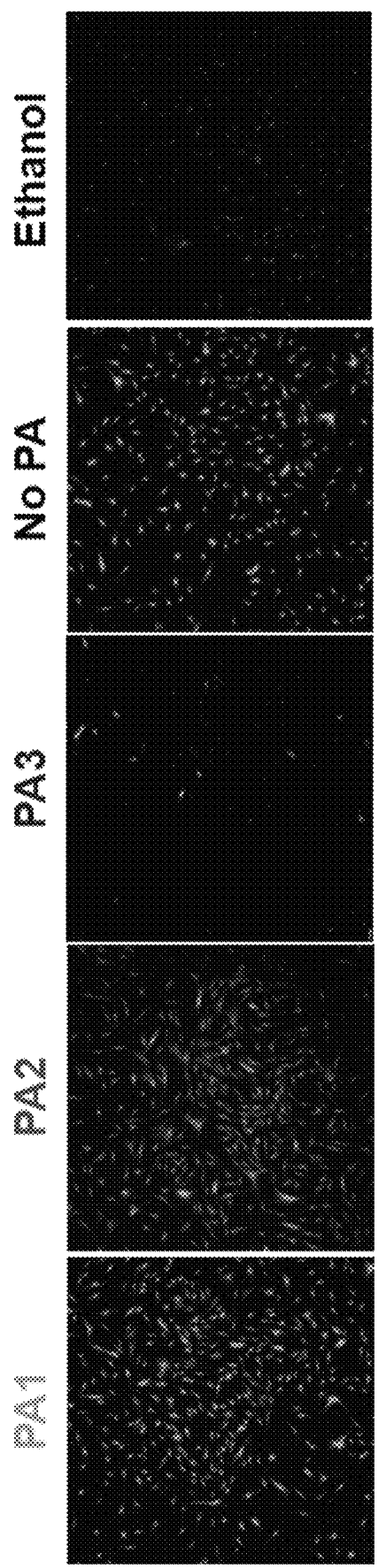
FIG. 13. Fluorescence imaging of live cells stained with calcein (green) and dead cells stained with ethidium homodimer (red) after 36 hour treatment with 100 μM PA1, PA2, or PA3 compared to cells with no PA treatment and cells with no PA treatment treated with 20% ethanol 30 minutes prior to staining.

Surface charge of PA structures is known to affect cell survival, with cationic PA molecules inducing cell death due to electrostatic interactions between their assemblies and cell membranes.[17,19] To test the cytocompatibility of the nonionic PA1, normal human lung fibroblast (nHLF) cultures were treated with PA solutions of various concentrations. Both PA1 and PA2 were highly cytocompatible, with over 85% of cells staining positive for calcein at up to 100 µM PA, whereas PA3 was highly cytotoxic ($EC_{50}$=25±4 µM). Thus, it was demonstrated that PA1 is a cytocompatibility alternative to PA3 for applications where negatively charged surfaces are undesirable (FIG. 12A, FIG. 13). Because only PA1 and PA2 were cytocompatible, a comparison of how PA1 and PA2 affect cell fate was evaluated in additional functional experiments.

Figure 14:
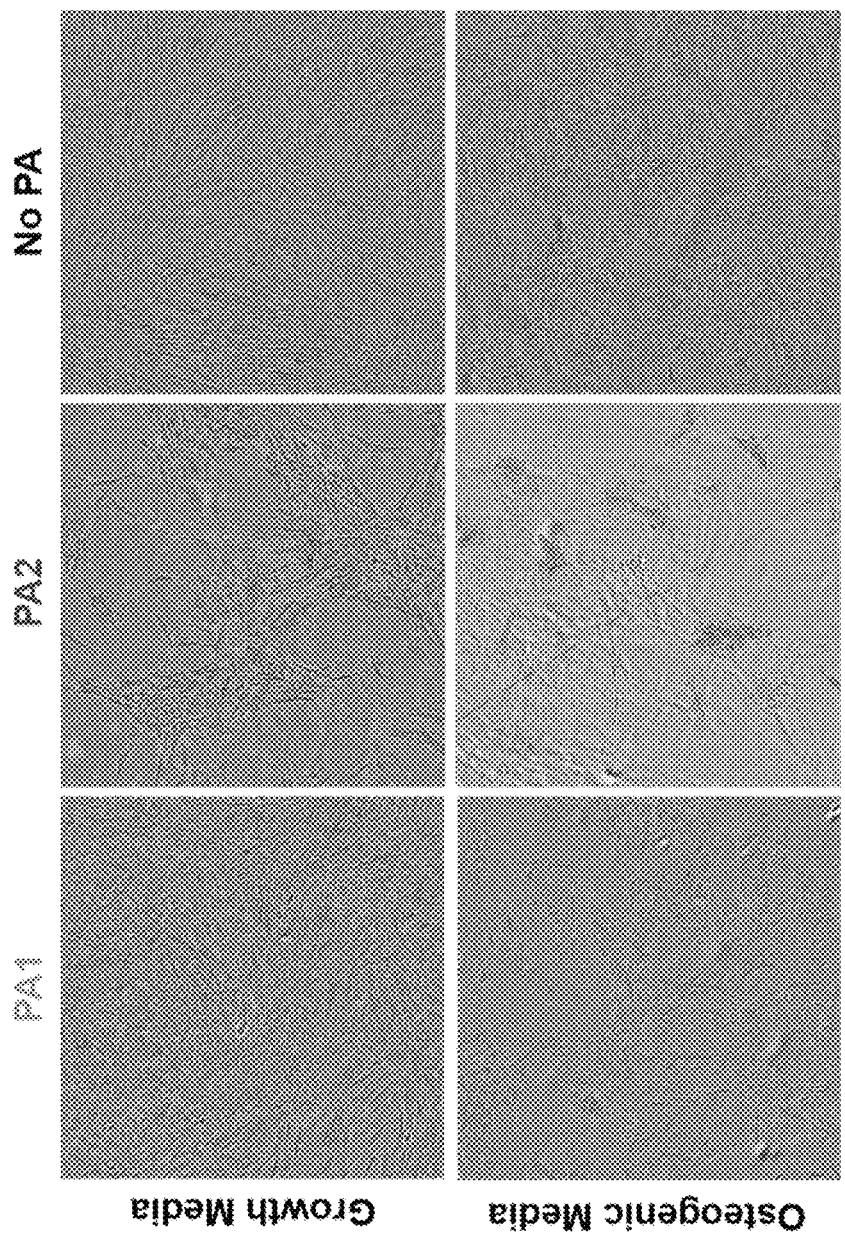
FIG. 14. Phase-contrast microscopy images of hMSCs cultured for seven days in growth media or in osteogenic media supplemented with 100 μM PA1, 100 μM PA2, and without PA added.

To determine how the presence of charged functional groups affected osteogenic differentiation, human MSCs cultured in either growth media or osteogenic media were treated with PA1 or PA2 at various concentrations for one week. In growth media, osteogenic differentiation as indicated by alkaline phosphatase (ALP) activity increased with increasing PA2 concentration, but was not affected by supplementation with PA1 This is likely due to the ability of anionic PA filaments to enhance growth factor signaling in vitro.[46] However, in osteogenic media supplemented with dexamethasone and β-glycerophosphate, the nonionic PA1 increased ALP activity with the largest increase when 10 µM PA was supplemented in the media, while PA2 did not affect differentiation (FIG. 12B, FIG. 14). To determine how co-assembling ionic and nonionic PAs affected MSC differentiation, human MSCs were cultured in the presence of PA1 and PA2 co-assemblies in osteogenic media. After 2 weeks, the greatest overall increase in osteogenesis was induced by a co-assembly of 25% PA2 with 75% PA1 (FIG. 12C). Based on these characterization studies, at this co-assembly ratio PA molecules formed more hydrated, ionic like assemblies, while maintaining a high surface density of PEGylated groups. It is hypothesized that increased spacing between PEG domains in these co-assemblies increases their ability to interact with cell surfaces and induce osteogenesis. Thus, both the overall charge of PA functional groups and the spatial orientation of those groups contribute to controlling osteogenic differentiation in response to the assemblies.

Figure 15:
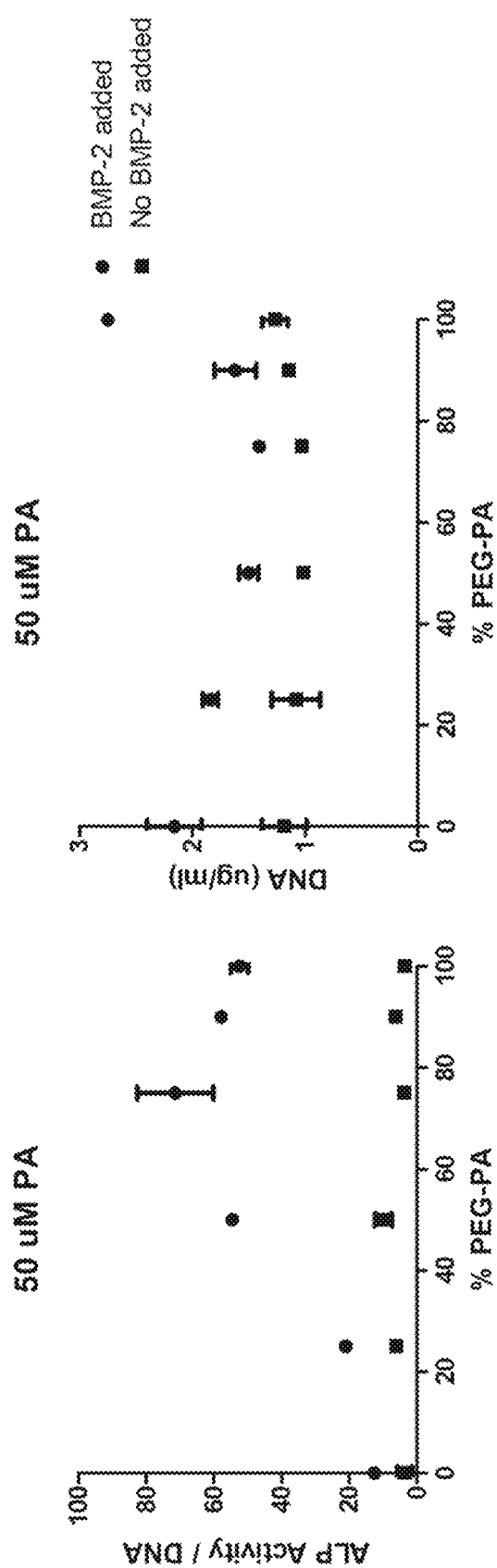
FIG. 15. ALP activity of MSCs cultured in varying co-assembly ratios of a $C16-V_2-A_2-E2$ peptide amphiphile (e.g. a charged PA) with the PEG-PA (PA1). 0% PEG-PA corresponds to 100% of the PA being $C16-V_2-A_2-E2$. Data shown include ALP activity (left panel) in the presence and absence of added growth factor BMP-2. The presence of the PEG-PA increases cell differentiation as measured by ALP activity.

FIG. 15 shows additional experiments using a co-assemblies of ionic and nonionic PAs with growth factor BMP-2 added to the cell culture. ALP activity of MSCs cultured in varying co-assembly ratios of a $C16-V_2-A2-E2$ peptide amphiphile (e.g. a charged PA) with the PEG-PA (PA1) are shown. 0% PEG-PA corresponds to 100% of the PA being $C16-V_2-A2-E2$. Data shown include ALP activity (left panel) in the presence and absence of added growth factor BMP-2. The data indicates that the presence of the PEG-PA increases cell differentiation as measured by ALP activity. Accordingly, the PEG-PA present in the co-assembly is shown to increase the bioactivity of BMP-2.

Conclusions

Described herein is a nonionic PEGylated PA that can self-assemble into similar nanofilaments at acidic, neutral, and basic pH with limited sensitivity to buffer ionic strength. Co-assembling these nonionic PA molecules with their charged counterparts produced a PA system with a tunable surface charge and demonstrated that only a minority of charged groups within an assembly are necessary to direct the morphology of the final assembly. Finally, it was shown that controlling charge can affect cell viability and osteogenic differentiation in response to the filaments. Accordingly, nonionic, filament forming PA molecules described herein may be used as a useful tool in applications where it is important to control electrostatic surface interactions or biodistribution of supramolecular PA structures.

REFERENCES

1. Hadjidemetriou, M.; Kostarelos, K., Nanomedicine: Evolution of the nanoparticle corona. *Nat Nanotechnol* 2017, 12 (4), 288-290.
2. Monopoli, M. P.; Aberg, C.; Salvati, A.; Dawson, K. A., Biomolecular coronas provide the biological identity of nanosized materials. *Nat Nanotechnol* 2012, 7 (12), 779-86.
3. Wang, H.-X.; Zuo, Z.-Q.; Du, J.-Z.; Wang, Y.-C.; Sun, R.; Cao, Z.-T.; Ye, X.-D.; Wang, J.-L.; Leong, K. W.; Wang, J., Surface charge critically affects tumor penetration and therapeutic efficacy of cancer nanomedicines. *Nano Today* 2016, 11 (2), 133-144.
4. Elci, S. G.; Jiang, Y.; Yan, B.; Kim, S. T.; Saha, K.; Moyano, D. F.; Yesilbag Tonga, G.; Jackson, L. C.; Rotello, V. M.; Vachet, R. W., Surface Charge Controls the Suborgan Biodistributions of Gold Nanoparticles. *ACS Nano* 2016, 10 (5), 5536-42.
5. Fröhlich, E., The role of surface charge in cellular uptake and cytotoxicity of medical nanoparticles. *International journal of nanomedicine* 2012, 7, 5577.
6. Yu, T.-T.; Cui, F.-Z.; Meng, Q.-Y.; Wang, J.; Wu, D.-C.; Zhang, J.; Kou, X.-X.; Yang, R.-L.; Liu, Y.; Zhang, Y. S.; Yang, F.; Zhou, Y.-H., Influence of Surface Chemistry on Adhesion and Osteo/Odontogenic Differentiation of Dental Pulp Stem Cells. *ACS Biomaterials Science & Engineering* 2017, 3 (6), 1119-1128.
7. Wang, Y.; Yao, S.; Meng, Q.; Yu, X.; Wang, X.; Cui, F., Gene expression profiling and mechanism study of neural stem cells response to surface chemistry. *Regen Biomater* 2014, 1 (1), 37-47.
8. Clemons, T. D.; Challenor, M.; Fitzgerald, M.; Dunlop, S. A.; Smith, N. M.; Iyer, K. S., Manipulating Cellular Interactions of Poly(glycidyl methacrylate) Nanoparticles Using Mixed Polymer Brushes. *ACS Macro Letters* 2016, 5 (10), 1132-1136.
9. Suk, J. S.; Xu, Q.; Kim, N.; Hanes, J.; Ensign, L. M., PEGylation as a strategy for improving nanoparticle-based drug and gene delivery. *Adv Drug Deliv Rev* 2016, 99 (Pt A), 28-51.
10. Webber, M. J.; Appel, E. A.; Vinciguerra, B.; Cortinas, A. B.; Thapa, L. S.; Jhunjhunwala, S.; Isaacs, L.; Langer, R.;

Anderson, D. G., Supramolecular PEGylation of biopharmaceuticals. *Proc Natl Acad Sci USA* 2016, 113 (50), 14189-14194.

11. Karakoti, A. S.; Das, S.; Thevuthasan, S.; Seal, S., PEGylated inorganic nanoparticles. *Angew Chem Int Ed Engl* 2011, 50 (9), 1980-94.

12. Hartgerink, J. D.; Beniash, E.; Stupp, S. I., Self-assembly and mineralization of peptide-amphiphile nanofibers. *Science* 2001, 294 (5547), 1684-8.

13. Hartgerink, J. D.; Beniash, E.; Stupp, S. I., Peptide-amphiphile nanofibers: a versatile scaffold for the preparation of self-assembling materials. *Proceedings of the National Academy of Sciences* 2002, 99 (8), 5133-5138.

14. <._Grifin-2012-Photodegradable Macromers and Hydrogels for Live Cell Encapsulation and Release.pdf>.

15. Cui, H.; Muraoka, T.; Cheetham, A. G.; Stupp, S. I., Self-Assembly of Giant Peptide Nanobelts. *Nano Letters* 2009, 9 (3), 945-951.

16. Ortony, J. H.; Newcomb, C. J.; Matson, J. B.; Palmer, L. C.; Doan, P. E.; Hoffman, B. M.; Stupp, S. I., Internal dynamics of a supramolecular nanofibre. Nature materials 2014, 13 (8), 812-816.

17. Tantakitti, F.; Boekhoven, J.; Wang, X.; Kazantsev, R. V.; Yu, T.; Li, J.; Zhuang, E.; Zandi, R.; Ortony, J. H.; Newcomb, C. J.; Palmer, L. C.; Shekhawat, G. S.; Olvera de la Cruz, M.; Schatz, G. C.; Stupp, S. I., Energy landscapes and functions of supramolecular systems. *Nat Mater* 2016, 15 (4), 469-76.

18. Edelbrock, A. N.; Àlvarez, Z.; Simkin, D.; Fyrner, T.; Chin, S. M.; Sato, K.; Kiskinis, E.; Stupp, S. I., Supramolecular Nanostructure Activates TrkB Receptor Signaling of Neuronal Cells by Mimicking Brain-Derived Neurotrophic Factor. *Nano letters* 2018, 18 (10), 6237-6247.

19. Newcomb, C. J.; Sur, S.; Ortony, J. H.; Lee, O. S.; Matson, J. B.; Boekhoven, J.; Yu, J. M.; Schatz, G. C.; Stupp, S. I., Cell death versus cell survival instructed by supramolecular cohesion of nanostructures. *Nature Communicaitons* 2014, 5, 3321.

20. Lee, S. S.; Fyrner, T.; Chen, F.; Alvarez, Z.; Sleep, E.; Chun, D. S.; Weiner, J. A.; Cook, R. W.; Freshman, R. D.; Schallmo, M. S.; Katchko, K. M.; Schneider, A. D.; Smith, J. T.; Yun, C.; Singh, G.; Hashmi, S. Z.; McClendon, M. T.; Yu, Z.; Stock, S. R.; Hsu, W. K.; Hsu, E. L.; Stupp, S. I., Sulfated glycopeptide nanostructures for multipotent protein activation. *Nature Nanotechnology* 2017, 12 (8), 821-829.

21. Cui, H.; Pashuck, E. T.; Velichko, Y. S.; Weigand, S. J.; Cheetham, A. G.; Newcomb, C. J.; Stupp, S. I., Spontaneous and x-ray-triggered crystallization at long range in self-assembling filament networks. *Science* 2010, 327 (5965), 555-9.

22. Iscen, A.; Schatz, G. C., Hofmeister Effects on Peptide Amphiphile Nanofiber Self-Assembly. *The Journal of Physical Chemistry B* 2019.

23. Gao, C.; Li, H.; Li, Y.; Kewalramani, S.; Palmer, L. C.; Dravid, V. P.; Stupp, S. I.; Olvera de la Cruz, M.; Bedzyk, M. J., Electrostatic Control of Polymorphism in Charged Amphiphile Assemblies. *Journal of Physical Chemistry B* 2017, 121 (7), 1623-1628.

24. Goldberger, J. E.; Berns, E. J.; Bitton, R.; Newcomb, C. J.; Stupp, S. I., Electrostatic control of bioactivity. *Angewandte Chemie International Edition* 2011, 50 (28), 6292-6295.

25. Moyer, T. J.; Finbloom, J. A.; Chen, F.; Toft, D. J.; Cryns, V. L.; Stupp, S. I., pH and amphiphilic structure direct supramolecular behavior in biofunctional assemblies. *J Am Chem Soc* 2014, 136 (42), 14746-52.

26. Zhang, S.; Greenfield, M. A.; Mata, A.; Palmer, L. C.; Bitton, R.; Mantei, J. R.; Aparicio, C.; Olvera de la Cruz, M.; Stupp, S. I., A self-assembly pathway to aligned monodomain gels. *Nat Mater* 2010, 9 (7), 594-601.

27. Greenfield, M. A.; Hoffman, J. R.; Olvera de la Cruz, M.; Stupp, S. I., Tunable mechanics of peptide nanofiber gels. *Langmuir* 2010, 26 (5), 3641-3647.

28. Behanna, H. A.; Donners, J. J.; Gordon, A. C.; Stupp, S. I., Coassembly of amphiphiles with opposite peptide polarities into nanofibers. *J Am Chem Soc* 2005, 127 (4), 1193-200.

29. Niece, K. L.; Hartgerink, J. D.; Donners, J. J.; Stupp, S. I., Self-assembly combining two bioactive peptide-amphiphile molecules into nanofibers by electrostatic attraction. *Journal of the American Chemical Society* 2003, 125 (24), 7146-7147.

30. Hamley, I.; Dehsorkhi, A.; Castelletto, V., Coassembly in binary mixtures of peptide amphiphiles containing oppositely charged residues. *Langmuir* 2013, 29 (16), 5050-5059.

31. Toksoz, S.; Mammadov, R.; Tekinay, A. B.; Guler, M. O., Electrostatic effects on nanofiber formation of self-assembling peptide amphiphiles. *J Colloid Interface Sci* 2011, 356 (1), 131-7.

32. Wan, Y.; Wang, Z.; Sun, J.; Li, Z., Extremely stable supramolecular hydrogels assembled from nonionic peptide amphiphiles. *Langmuir* 2016, 32 (30), 7512-7518.

33. Chen, C.; Wu, D.; Fu, W.; Li, Z., Peptide hydrogels assembled from nonionic alkyl-polypeptide amphiphiles prepared by ring-opening polymerization. Biomacromolecules 2013, 14 (8), 2494-8.

34. Sur, S.; Tantakitti, F.; Matson, J. B.; Stupp, S. I., Epitope topography controls bioactivity in supramolecular nanofibers. *Biomaterials Science* 2015, 3 (3), 520-532.

35. Freeman, R.; Han, M.; Alvarez, Z.; Lewis, J. A.; Wester, J. R.; Stephanopoulos, N.; McClendon, M. T.; Lynsky, C.; Godbe, J. M.; Sangji, H.; Luijten, E.; Stupp, S. I., Reversible self-assembly of superstructured networks. *Science* 2018, 362 (6416), 808-813.

36. Toft, D. J.; Moyer, T. J.; Standley, S. M.; Ruff, Y.; Ugolkov, A.; Stupp, S. I.; Cryns, V. L., Coassembled cytotoxic and pegylated peptide amphiphiles form filamentous nanostructures with potent antitumor activity in models of breast cancer. *ACS nano* 2012, 6 (9), 7956-7965.

37. Hamley, I.; Ansari, I.; Castelletto, V.; Nuhn, H.; Rosier, A.; Klok, H.-A., Solution self-assembly of hybrid block copolymers containing poly (ethylene glycol) and amphiphilic β-strand peptide sequences. *Biomacromolecules* 2005, 6 (3), 1310-1315.

38. Perinelli, D. R.; Campana, M.; Singh, I.; Vllasaliu, D.; Doutch, J.; Palmieri, G. F.; Casettari, L., PEGylation affects the self-assembling behavior of amphiphilic octapeptides. *International Journal of Pharmaceutics* 2019, 118752.

39. Stuart, M. C. A.; van de Pas, J. C.; Engberts, J. B. F. N., The use of Nile Red to monitor the aggregation behavior in ternary surfactant-water-organic solvent systems. *Journal of Physical Organic Chemistry* 2005, 18 (9), 929-934.

40. Niece, K. L.; Czeisler, C.; Sahni, V.; Tysseling-Mattiace, V.; Pashuck, E. T.; Kessler, J. A.; Stupp, S. I., Modification of gelation kinetics in bioactive peptide amphiphiles. *Biomaterials* 2008, 29 (34), 4501-9.

41. Zhang, H.; Yu, M.; Song, A.; Song, Y.; Xin, X.; Shen, J.; Yuan, S., Modulating hierarchical self-assembly behavior of a peptide amphiphile/nonionic surfactant mixed system. *RSC Advances* 2016, 6 (11), 9186-9193.

42. Mukherjee, S.; Chowdhury, P.; Gai, F., Infrared study of the effect of hydration on the amide I band and aggregation properties of helical peptides. *J Phys Chem B* 2007, 111 (17), 4596-602.

43. Tew, L. S.; Ching, J. Y.; Ngalim, S. H.; Khung, Y. L., Driving mesenchymal stem cell differentiation from self-assembled monolayers. *Rsc Advances* 2018, 8 (12), 6551-6564.

44. Li, J. J.; Kawazoe, N.; Chen, G., Gold nanoparticles with different charge and moiety induce differential cell response on mesenchymal stem cell osteogenesis. *Biomaterials* 2015, 54, 226-36.

45. Shrestha, S.; Mao, Z.; Fedutik, Y.; Gao, C., Influence of titanium dioxide nanorods with different surface chemistry on the differentiation of rat bone marrow mesenchymal stem cells. *J Mater Chem B* 2016, 4 (43), 6955-6966.

46. Lee, S. S.; Hsu, E. L.; Mendoza, M.; Ghodasra, J.; Nickoli, M. S.; Ashtekar, A.;

Polavarapu, M.; Babu, J.; Riaz, R. M.; Nicolas, J. D.; Nelson, D.; Hashmi, S. Z.; Kaltz, S. R.; Earhart, J. S.; Merk, B. R.; McKee, J. S.; Bairstow, S. F.; Shah, R. N.; Hsu, W. K.; Stupp, S. I., Gel scaffolds of BMP-2-binding peptide amphiphile nanofibers for spinal arthrodesis. *Adv Healthc Mater* 2015, 4 (1), 131-141.

It is understood that the foregoing detailed description and accompanying examples are merely illustrative and are not to be taken as limitations upon the scope of the disclosure, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the disclosure, may be made without departing from the spirit and scope thereof.

Any patents and publications referenced herein are herein incorporated by reference in their entireties.

The invention claimed is:

1. A peptide amphiphile comprising a hydrophobic tail, a structural peptide segment, and a PEG domain, wherein the peptide amphiphile is nonionic.

2. The peptide amphiphile of claim 1, wherein the hydrophobic tail comprises an 8-24 carbon alkyl chain ($C_{8-24}$).

3. The peptide amphiphile of claim 1, wherein the structural peptide segment has a propensity for forming β-sheet conformations.

4. The peptide amphiphile of claim 3, wherein the structural peptide segment comprises $V_2A_2$ or $V_3A_3$.

5. The peptide amphiphile of claim 1, wherein the PEG domain comprises a PEG containing 1-20 repeating ethylene glycol subunits.

6. The peptide amphiphile of claim 5, wherein the PEG contains 10 repeating ethylene glycol subunits.

7. The peptide amphiphile of claim 1, further comprising a growth factor binding sequence.

8. The peptide amphiphile of claim 7, wherein the growth factor binding sequence binds to a TGF-β family protein.

9. The peptide amphiphile of claim 8, wherein the growth factor binding sequence comprises the peptide sequence HSNGLPL.

10. A nanofiber comprising the peptide amphiphile of claim 1.

11. The nanofiber of claim 10, further comprising one or more charged peptide amphiphiles, wherein the charged peptide amphiphiles comprise a hydrophobic tail, a structural peptide segment, and a charged peptide segment.

12. The nanofiber of claim 11, wherein the charged segment is anionic.

13. The nanofiber of claim 12, wherein the charged segment comprises $E_{2-4}$.

14. The nanofiber of claim 11, further comprising at least one growth factor protein or a mimetic thereof.

15. The nanofiber of claim 14, wherein the growth factor protein or mimetic thereof is bound to the charged peptide amphiphile.

16. The nanofiber of claim 15, wherein the growth factor protein is a TGF-β family protein.

17. A composition comprising the nanofiber of claim 10.

18. A method comprising contacting a cell with the composition of claim 17.

19. A method comprising providing the composition of claim 17 to a subject in need thereof.

20. The method of claim 19, wherein the composition promotes regeneration of one or more damaged bones or tissues in the subject.

* * * * *

UNITED STATES PATENT AND TRADEMARK OFFICE
CERTIFICATE OF CORRECTION

| | | |
|---|---|---|
| PATENT NO. | : 11,998,589 B2 | Page 1 of 1 |
| APPLICATION NO. | : 17/374287 | |
| DATED | : June 4, 2024 | |
| INVENTOR(S) | : Jacob A. Lewis, Ronit Freeman and Samuel I. Stupp | |

It is certified that error appears in the above-identified patent and that said Letters Patent is hereby corrected as shown below:

In the Claims

Claim 3, Column 37, Line 8 reads:
"tural peptide segment has a propensity for forming (3-sheet"
Whereas it should read:
"tural peptide segment has a propensity for forming β-sheet"

Signed and Sealed this
Thirtieth Day of July, 2024

*Katherine Kelly Vidal*

Katherine Kelly Vidal
*Director of the United States Patent and Trademark Office*

SEQUENCE LISTING

```
<160> NUMBER OF SEQ ID NOS: 22

<210> SEQ ID NO 1
<211> LENGTH: 7
<212> TYPE: PRT
<213> ORGANISM: Artificial sequence
<220> FEATURE:
<223> OTHER INFORMATION: synthetic

<400> SEQUENCE: 1

His Ser Asn Gly Leu Pro Leu
1               5

<210> SEQ ID NO 2
<211> LENGTH: 7
<212> TYPE: PRT
<213> ORGANISM: Artificial sequence
<220> FEATURE:
<223> OTHER INFORMATION: synthetic

<400> SEQUENCE: 2

Leu Pro Leu Gly Asn Ser His
1               5

<210> SEQ ID NO 3
<211> LENGTH: 7
<212> TYPE: PRT
<213> ORGANISM: Artificial sequence
<220> FEATURE:
<223> OTHER INFORMATION: synthetic

<400> SEQUENCE: 3

Leu Arg Asn Tyr Ser His Ser
1               5

<210> SEQ ID NO 4
<211> LENGTH: 7
<212> TYPE: PRT
<213> ORGANISM: Artificial sequence
<220> FEATURE:
<223> OTHER INFORMATION: synthetic

<400> SEQUENCE: 4

Val Tyr Arg His Leu Pro Thr
1               5
```

<210> SEQ ID NO 5
<211> LENGTH: 7
<212> TYPE: PRT
<213> ORGANISM: Artificial sequence
<220> FEATURE:
<223> OTHER INFORMATION: synthetic

<400> SEQUENCE: 5

Arg Val Ser Thr Trp Asp Thr
1               5

<210> SEQ ID NO 6
<211> LENGTH: 7
<212> TYPE: PRT
<213> ORGANISM: Artificial sequence
<220> FEATURE:
<223> OTHER INFORMATION: synthetic

<400> SEQUENCE: 6

Pro Ala Pro Arg Trp Ile His
1               5

<210> SEQ ID NO 7
<211> LENGTH: 7
<212> TYPE: PRT
<213> ORGANISM: Artificial sequence
<220> FEATURE:
<223> OTHER INFORMATION: synthetic

<400> SEQUENCE: 7

Arg Thr Thr Ser Pro Thr Ala
1               5

<210> SEQ ID NO 8
<211> LENGTH: 7
<212> TYPE: PRT
<213> ORGANISM: Artificial sequence
<220> FEATURE:
<223> OTHER INFORMATION: synthetic

<400> SEQUENCE: 8

Gly Lys Tyr Pro Pro Thr Ser
1               5

<210> SEQ ID NO 9
<211> LENGTH: 7
<212> TYPE: PRT
<213> ORGANISM: Artificial sequence
<220> FEATURE:
<223> OTHER INFORMATION: synthetic

<400> SEQUENCE: 9

Ala Trp Lys Ser Val Thr Ala
1               5

<210> SEQ ID NO 10
<211> LENGTH: 7
<212> TYPE: PRT
<213> ORGANISM: Artificial sequence
<220> FEATURE:
<223> OTHER INFORMATION: synthetic

<400> SEQUENCE: 10

Leu Pro Ser Pro Ile Gln Lys
1               5

```
<210> SEQ ID NO 11
<211> LENGTH: 7
<212> TYPE: PRT
<213> ORGANISM: Artificial sequence
<220> FEATURE:
<223> OTHER INFORMATION: synthetic

<400> SEQUENCE: 11

Tyr Pro Val His Pro Ser Thr
1               5

<210> SEQ ID NO 12
<211> LENGTH: 7
<212> TYPE: PRT
<213> ORGANISM: Artificial sequence
<220> FEATURE:
<223> OTHER INFORMATION: synthetic

<400> SEQUENCE: 12

Leu His Tyr Pro Phe Met Thr
1               5

<210> SEQ ID NO 13
<211> LENGTH: 7
<212> TYPE: PRT
<213> ORGANISM: Artificial sequence
<220> FEATURE:
<223> OTHER INFORMATION: synthetic

<400> SEQUENCE: 13

Lys Gln Ala Leu Thr Gln Thr
1               5

<210> SEQ ID NO 14
<211> LENGTH: 7
<212> TYPE: PRT
<213> ORGANISM: Artificial sequence
<220> FEATURE:
<223> OTHER INFORMATION: synthetic

<400> SEQUENCE: 14

Trp Pro Ala Leu Phe Thr His
1               5

<210> SEQ ID NO 15
<211> LENGTH: 7
<212> TYPE: PRT
<213> ORGANISM: Artificial sequence
<220> FEATURE:
<223> OTHER INFORMATION: synthetic

<400> SEQUENCE: 15

Pro Gly Pro Thr Val Gln Gly
1               5

<210> SEQ ID NO 16
<211> LENGTH: 7
<212> TYPE: PRT
<213> ORGANISM: Artificial sequence
<220> FEATURE:
<223> OTHER INFORMATION: synthetic

<400> SEQUENCE: 16

Leu His Tyr Pro Phe Met Thr
1               5

<210> SEQ ID NO 17
```

```
<211> LENGTH: 7
<212> TYPE: PRT
<213> ORGANISM: Artificial sequence
<220> FEATURE:
<223> OTHER INFORMATION: synthetic

<400> SEQUENCE: 17

Gln Gln Thr Gln Ala Gln His
1               5

<210> SEQ ID NO 18
<211> LENGTH: 7
<212> TYPE: PRT
<213> ORGANISM: Artificial sequence
<220> FEATURE:
<223> OTHER INFORMATION: synthetic

<400> SEQUENCE: 18

Pro Ile Gln Pro Asp Glu Arg
1               5

<210> SEQ ID NO 19
<211> LENGTH: 7
<212> TYPE: PRT
<213> ORGANISM: Artificial sequence
<220> FEATURE:
<223> OTHER INFORMATION: synthetic

<400> SEQUENCE: 19

Pro Phe Asp Pro Pro Val Arg
1               5

<210> SEQ ID NO 20
<211> LENGTH: 7
<212> TYPE: PRT
<213> ORGANISM: Artificial sequence
<220> FEATURE:
<223> OTHER INFORMATION: synthetic

<400> SEQUENCE: 20

Asp Val Ser Pro Ala Tyr His
1               5

<210> SEQ ID NO 21
<211> LENGTH: 15
<212> TYPE: PRT
<213> ORGANISM: Artificial sequence
<220> FEATURE:
<223> OTHER INFORMATION: synthetic

<400> SEQUENCE: 21

Ile Gly Lys Tyr Lys Leu Gln Tyr Leu Glu Gln Trp Thr Leu Lys
1               5                   10                  15

<210> SEQ ID NO 22
<211> LENGTH: 15
<212> TYPE: PRT
<213> ORGANISM: Artificial sequence
<220> FEATURE:
<223> OTHER INFORMATION: synthetic

<400> SEQUENCE: 22

Ile Gly Lys Tyr Lys Leu Gln Tyr Leu Glu Gln Trp Thr Leu Lys
1               5                   10                  15
```